United States Patent
Dos Santos

(10) Patent No.: US 8,372,036 B2
(45) Date of Patent: Feb. 12, 2013

(54) MULTI-LAYER HEAT ASSEMBLY FOR A DRUG DELIVERY DEVICE

(75) Inventor: Cesario Pereira Dos Santos, Aliso Viejo, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 405 days.

(21) Appl. No.: 12/774,363

(22) Filed: May 5, 2010

(65) Prior Publication Data

US 2010/0286632 A1 Nov. 11, 2010

Related U.S. Application Data

(60) Provisional application No. 61/175,813, filed on May 6, 2009, provisional application No. 61/289,467, filed on Dec. 23, 2009.

(51) Int. Cl.
*A61F 7/12* (2006.01)
*A61M 5/00* (2006.01)
*A61M 35/00* (2006.01)
*E21B 7/15* (2006.01)
*A61C 19/00* (2006.01)

(52) U.S. Cl. ........ 604/113; 604/114; 604/181; 604/294; 392/304; 433/32

(58) Field of Classification Search .......... 604/112–114, 604/21, 294, 181; 392/304, 308, 311, 314; 433/32; 606/27–28
See application file for complete search history.

(56) References Cited

U.S. PATENT DOCUMENTS

| | | | |
|---|---|---|---|
| 640,868 A | 1/1900 | Bring | |
| 1,039,591 A | 9/1912 | Prideaux | |
| 1,252,614 A | 1/1918 | Pieper | |
| 1,609,424 A | 12/1926 | Paul | |
| 2,124,293 A | * 7/1938 | Goldstein | ............ 604/114 |
| 2,591,457 A | 4/1952 | Maynes | |
| 2,661,871 A | 12/1953 | Huenergardt | |
| 2,826,339 A | 3/1958 | Maillard | |
| 2,847,996 A | 8/1958 | Cohen et al. | |
| 3,089,815 A | 5/1963 | Lieb et al. | |
| 3,166,221 A | 1/1965 | Nielsen | |
| 3,199,740 A | 8/1965 | Huffa et al. | |
| 3,311,265 A | 3/1967 | Creighton, Jr. et al. | |

(Continued)

FOREIGN PATENT DOCUMENTS

| | | |
|---|---|---|
| CA | 1313802 | 2/1993 |
| DE | 3434930 A1 | 4/1986 |

(Continued)

OTHER PUBLICATIONS

Business Wire Via First!, "Bausch & Lomb and Control Delivery Systems Agree to Develop Breakthrough Therapeutic Products for Severe Eye Diseases," NewsEdge Corp., Jun. 15, 1989, 4 pgs.

(Continued)

*Primary Examiner* — Kevin C Sirmons
*Assistant Examiner* — Bradley G Thomas, Jr.
(74) *Attorney, Agent, or Firm* — Russell Henrichs

(57) ABSTRACT

In various embodiments, an ophthalmic injection device may include a dispensing chamber to hold a substance (e.g., a drug) to be injected into an eye, a thermal feedback layer with at least one thermal sensor, and a temperature control layer to apply or remove heat from the dispensing chamber. In some embodiments, the thermal feedback layer and the temperature control layer may be coupled to each other and/or coupled to the dispensing chamber. In some embodiments, at least one of the thermal sensors may be secured between the temperature control layer and the dispensing chamber using a thermal adhesive.

7 Claims, 24 Drawing Sheets

U.S. PATENT DOCUMENTS

| | | | |
|---|---|---|---|
| 3,416,530 A | 12/1968 | Ness | |
| 3,439,675 A | 4/1969 | Cohen | |
| 3,608,549 A | 9/1971 | Merrill | |
| 3,767,085 A | 10/1973 | Cannon et al. | |
| 3,828,777 A | 8/1974 | Ness | |
| 3,828,980 A | 8/1974 | Creighton et al. | |
| 3,835,835 A | 9/1974 | Thompson et al. | |
| 3,858,581 A | 1/1975 | Kamen | |
| 3,892,537 A | 7/1975 | Gulati et al. | |
| 3,952,920 A | 4/1976 | Bergman | |
| 3,982,537 A | 9/1976 | Bucalo | |
| 4,007,742 A | 2/1977 | Banko | |
| 4,014,335 A | 3/1977 | Arnold | |
| 4,030,499 A | 6/1977 | Bucalo | |
| 4,046,288 A | 9/1977 | Bergman | |
| 4,054,138 A | 10/1977 | Bucalo | |
| 4,109,653 A | 8/1978 | Kozam et al. | |
| 4,122,850 A | 10/1978 | Bucalo | |
| 4,184,510 A | 1/1980 | Murry et al. | |
| 4,246,932 A | 1/1981 | Raines | |
| 4,260,077 A | 4/1981 | Schroeder | |
| 4,265,618 A | 5/1981 | Herskovitz et al. | |
| 4,300,557 A | 11/1981 | Refojo et al. | |
| 4,327,725 A | 5/1982 | Cortese et al. | |
| 4,357,136 A | 11/1982 | Herskovitz et al. | |
| 4,367,737 A | 1/1983 | Kozam et al. | |
| 4,392,827 A | 7/1983 | Martin | |
| 4,453,934 A | 6/1984 | Gahwiler et al. | |
| 4,464,174 A | 8/1984 | Ennis | |
| 4,471,888 A | 9/1984 | Herb et al. | |
| 4,474,752 A | 10/1984 | Haslam et al. | |
| 4,484,915 A | 11/1984 | Tartaglia | |
| 4,582,488 A * | 4/1986 | Newman | 433/81 |
| 4,608,042 A | 8/1986 | Venderveen et al. | |
| 4,609,371 A | 9/1986 | Pizzino | |
| 4,610,666 A | 9/1986 | Pizzino | |
| 4,684,344 A | 8/1987 | Brockway et al. | |
| 4,704,088 A | 11/1987 | Newman | |
| 4,709,135 A * | 11/1987 | Dietrich et al. | 392/470 |
| 4,713,446 A | 12/1987 | DeVore et al. | |
| 4,759,746 A | 7/1988 | Straus | |
| 4,764,165 A | 8/1988 | Reimels et al. | |
| 4,792,329 A | 12/1988 | Schreuder | |
| 4,795,423 A | 1/1989 | Osterholm | |
| 4,830,855 A | 5/1989 | Stewart | |
| 4,834,714 A | 5/1989 | Lascar et al. | |
| 4,853,224 A | 8/1989 | Wong | |
| 4,911,161 A | 3/1990 | Schechter | |
| 4,911,328 A | 3/1990 | Keller | |
| 4,946,450 A | 8/1990 | Erwin | |
| 4,949,874 A | 8/1990 | Fiedler | |
| 4,992,045 A | 2/1991 | Beisel | |
| 4,997,652 A | 3/1991 | Wong | |
| 5,000,955 A | 3/1991 | Gould et al. | |
| 5,005,735 A | 4/1991 | Keller | |
| 5,066,276 A | 11/1991 | Wang | |
| 5,120,307 A | 6/1992 | Wang | |
| 5,127,831 A | 7/1992 | Bab | |
| 5,147,647 A | 9/1992 | Darougar | |
| 5,164,188 A | 11/1992 | Wong | |
| 5,167,618 A | 12/1992 | Kershner | |
| 5,174,475 A | 12/1992 | Day et al. | |
| 5,178,635 A | 1/1993 | Gwon et al. | |
| 5,224,628 A | 7/1993 | Keller | |
| RE34,487 E | 12/1993 | Keller | |
| 5,290,259 A | 3/1994 | Fischer | |
| 5,300,114 A | 4/1994 | Gwon et al. | |
| 5,322,691 A | 6/1994 | Darougar et al. | |
| 5,324,305 A | 6/1994 | Kanner | |
| 5,328,481 A | 7/1994 | Wang | |
| 5,336,175 A | 8/1994 | Mames | |
| 5,360,413 A | 11/1994 | Leason et al. | |
| 5,370,630 A | 12/1994 | Smidebush et al. | |
| 5,378,475 A | 1/1995 | Smith et al. | |
| 5,403,901 A | 4/1995 | Namdaran et al. | |
| 5,423,752 A | 6/1995 | Haber et al. | |
| 5,431,630 A | 7/1995 | Leonard | |
| 5,443,505 A | 8/1995 | Wong et al. | |
| 5,454,268 A | 10/1995 | Kim | |
| 5,466,466 A | 11/1995 | Muller | |
| 5,476,511 A | 12/1995 | Gwon et al. | |
| 5,478,323 A | 12/1995 | Westwood et al. | |
| 5,487,725 A | 1/1996 | Peyman | |
| 5,516,522 A | 5/1996 | Peyman et al. | |
| 5,568,883 A | 10/1996 | Cataneo et al. | |
| 5,582,595 A | 12/1996 | Haber et al. | |
| 5,584,815 A | 12/1996 | Pawelka et al. | |
| 5,602,188 A | 2/1997 | Nakanishi | |
| 5,620,700 A | 4/1997 | Berggren et al. | |
| 5,632,984 A | 5/1997 | Wong et al. | |
| 5,662,612 A | 9/1997 | Niehoff | |
| 5,665,069 A | 9/1997 | Cumer et al. | |
| 5,679,666 A | 10/1997 | Clark | |
| 5,722,956 A | 3/1998 | Sims et al. | |
| 5,725,493 A | 3/1998 | Avery et al. | |
| 5,743,274 A | 4/1998 | Peyman | |
| 5,743,886 A | 4/1998 | Lynn et al. | |
| 5,766,242 A | 6/1998 | Wong et al. | |
| 5,766,619 A | 6/1998 | Aiache et al. | |
| 5,770,592 A | 6/1998 | Clark | |
| 5,773,019 A | 6/1998 | Ashton et al. | |
| 5,783,205 A | 7/1998 | Berggren et al. | |
| 5,792,103 A | 8/1998 | Schwartz et al. | |
| 5,797,898 A | 8/1998 | Santini, Jr. et al. | |
| 5,817,075 A | 10/1998 | Guingo | |
| 5,824,072 A | 10/1998 | Wong | |
| 5,824,073 A | 10/1998 | Peyman | |
| 5,830,173 A | 11/1998 | Avery et al. | |
| 5,836,935 A | 11/1998 | Ashton et al. | |
| 5,860,949 A | 1/1999 | Chen | |
| 5,882,338 A | 3/1999 | Gray | |
| 5,902,598 A | 5/1999 | Chen et al. | |
| 5,904,144 A | 5/1999 | Hammang et al. | |
| 5,916,584 A | 6/1999 | O'Donoghue et al. | |
| 5,928,197 A | 7/1999 | Niehoff | |
| 5,928,663 A | 7/1999 | Peyman | |
| 5,954,695 A | 9/1999 | Sims et al. | |
| 5,984,889 A | 11/1999 | Christ et al. | |
| 6,001,386 A | 12/1999 | Ashton et al. | |
| 6,028,099 A | 2/2000 | de Juan, Jr. | |
| 6,047,861 A | 4/2000 | Vidal et al. | |
| 6,051,011 A | 4/2000 | Weidenbenner | |
| 6,074,661 A | 6/2000 | Olejnik et al. | |
| 6,126,687 A | 10/2000 | Peyman | |
| 6,135,984 A | 10/2000 | Dishler | |
| 6,165,190 A | 12/2000 | Nguyen | |
| 6,210,357 B1 | 4/2001 | Morris | |
| 6,221,045 B1 | 4/2001 | Duchon et al. | |
| 6,270,343 B1 | 8/2001 | Martin | |
| 6,290,690 B1 | 9/2001 | Huculak et al. | |
| 6,299,603 B1 | 10/2001 | Hecker et al. | |
| 6,352,522 B1 | 3/2002 | Kim et al. | |
| 6,364,865 B1 | 4/2002 | Lavi et al. | |
| 6,372,245 B1 | 4/2002 | Bowman et al. | |
| 6,378,526 B1 | 4/2002 | Bowman et al. | |
| 6,397,849 B1 | 6/2002 | Bowman et al. | |
| 6,413,245 B1 | 7/2002 | Yaacobi et al. | |
| 6,416,777 B1 | 7/2002 | Yaacobi | |
| 6,419,656 B1 | 7/2002 | Vetter et al. | |
| 6,436,143 B1 | 8/2002 | Ross et al. | |
| 6,488,659 B1 | 12/2002 | Rosenman | |
| 6,520,930 B2 | 2/2003 | Critchlow et al. | |
| 6,537,246 B1 | 3/2003 | Unger et al. | |
| 6,569,113 B2 | 5/2003 | Wirt et al. | |
| 6,585,700 B1 | 7/2003 | Trocki et al. | |
| 6,595,979 B1 | 7/2003 | Epstein et al. | |
| 6,613,024 B1 | 9/2003 | Gargione | |
| 6,635,267 B1 | 10/2003 | Miyoshi et al. | |
| 6,645,179 B1 | 11/2003 | Ishikawa et al. | |
| 6,723,074 B1 | 4/2004 | Halseth | |
| 6,726,654 B2 | 4/2004 | Rosenman | |
| 6,732,887 B2 | 5/2004 | Bills | |
| 6,940,209 B2 | 9/2005 | Henderson | |
| 6,991,457 B2 * | 1/2006 | Kazen et al. | 433/32 |
| 7,176,030 B2 | 2/2007 | Faries, Jr. et al. | |
| 7,740,619 B2 * | 6/2010 | Pinedjian et al. | 604/220 |
| 7,762,981 B2 | 7/2010 | Dacquay et al. | |

| Patent No. | Date | Inventors | Class |
|---|---|---|---|
| 7,815,603 B2 * | 10/2010 | Dacquay et al. | 604/131 |
| 7,871,399 B2 | 1/2011 | Dacquay et al. | |
| 7,887,517 B2 | 2/2011 | Santos et al. | |
| 7,887,521 B2 * | 2/2011 | Dacquay et al. | 604/294 |
| 2002/0042591 A1 | 4/2002 | Muhlbauer et al. | |
| 2002/0055720 A1 | 5/2002 | Hohlfelder et al. | |
| 2003/0055380 A1 | 3/2003 | Flaherty | |
| 2003/0125665 A1 | 7/2003 | Rosenman | |
| 2004/0013704 A1 | 1/2004 | Kebra et al. | |
| 2004/0039253 A1 | 2/2004 | Peyman et al. | |
| 2004/0052761 A1 | 3/2004 | Vernon et al. | |
| 2004/0054319 A1 | 3/2004 | Langley et al. | |
| 2004/0064102 A1 | 4/2004 | Yamada | |
| 2004/0133155 A1 | 7/2004 | Varner et al. | |
| 2004/0167466 A1 | 8/2004 | Drasler et al. | |
| 2004/0167480 A1 | 8/2004 | Bos | |
| 2004/0176720 A1 | 9/2004 | Kipfer | |
| 2004/0210200 A1 | 10/2004 | Gerondale et al. | |
| 2004/0231667 A1 | 11/2004 | Horton et al. | |
| 2005/0015056 A1 | 1/2005 | Duchon et al. | |
| 2005/0065477 A1 | 3/2005 | Jost | |
| 2005/0177137 A1 | 8/2005 | Kipfer | |
| 2006/0047250 A1 | 3/2006 | Hickingbotham | |
| 2006/0110428 A1 | 5/2006 | deJuan et al. | |
| 2007/0016186 A1 | 1/2007 | LoRusso | |
| 2007/0038174 A1 | 2/2007 | Hopkins | |
| 2007/0060887 A1 | 3/2007 | Marsh et al. | |
| 2007/0142769 A1 | 6/2007 | Griffiths et al. | |
| 2007/0244442 A1 | 10/2007 | Chowhan | |
| 2007/0268340 A1 | 11/2007 | Dacquay et al. | |
| 2007/0270744 A1 | 11/2007 | Dacquay et al. | |
| 2007/0270750 A1 | 11/2007 | Dacquay et al. | |
| 2007/0282282 A1 | 12/2007 | Wong et al. | |
| 2007/0293820 A1 | 12/2007 | Dacquay et al. | |
| 2008/0015545 A1 | 1/2008 | Sanchez, Jr. | |
| 2008/0021412 A1 | 1/2008 | Dos Santos et al. | |
| 2008/0021419 A1 | 1/2008 | Dacquay et al. | |
| 2008/0021438 A1 | 1/2008 | Dacquay et al. | |
| 2008/0097379 A1 | 4/2008 | Dacquay et al. | |
| 2008/0161757 A1 | 7/2008 | Nayak et al. | |
| 2008/0281292 A1 | 11/2008 | Hickingbotham et al. | |
| 2009/0036842 A1 | 2/2009 | Pinedjian | |
| 2009/0036846 A1 | 2/2009 | Dacquay et al. | |
| 2009/0093788 A1 | 4/2009 | Sanchez, Jr. | |
| 2009/0093789 A1 | 4/2009 | Dacquay et al. | |
| 2009/0177182 A1 * | 7/2009 | Hickingbotham et al. | 604/506 |
| 2009/0227979 A1 | 9/2009 | Sanchez, Jr. | |
| 2009/0254045 A1 | 10/2009 | Jost | |
| 2009/0287150 A1 | 11/2009 | Dacquay et al. | |
| 2010/0030136 A1 | 2/2010 | Dacquay et al. | |
| 2010/0057003 A1 | 3/2010 | Dos Santos | |
| 2010/0069842 A1 | 3/2010 | Dos Santos et al. | |
| 2010/0106083 A1 | 4/2010 | Dacquay et al. | |
| 2010/0106089 A1 | 4/2010 | Santos et al. | |
| 2010/0137785 A1 | 6/2010 | Lind | |
| 2010/0152676 A1 | 6/2010 | Clements et al. | |
| 2010/0160870 A1 | 6/2010 | Clements et al. | |
| 2010/0211044 A1 | 8/2010 | Dacquay et al. | |
| 2010/0286632 A1 | 11/2010 | Dos Santos et al. | |
| 2010/0286654 A1 | 11/2010 | Dos Santos et al. | |

FOREIGN PATENT DOCUMENTS

| | | |
|---|---|---|
| EP | 0348146 A1 | 12/1989 |
| EP | 0356372 A2 | 2/1990 |
| EP | 0356372 A3 | 3/1990 |
| EP | 0398394 A2 | 11/1990 |
| EP | 0398394 A3 | 12/1990 |
| EP | 0520443 A2 | 12/1992 |
| EP | 0398394 B1 | 10/1993 |
| EP | 0520443 A3 | 3/1994 |
| EP | 0356372 B1 | 6/1994 |
| EP | 0520443 B1 | 1/1997 |
| EP | 0904787 A1 | 3/1999 |
| EP | 1704840 A1 | 9/2006 |
| EP | 1704840 B1 | 1/2008 |
| GB | 1551767 | 8/1979 |
| JP | 2002/059055 A | 2/2002 |
| WO | WO 82/03761 A1 | 11/1982 |
| WO | WO 87/00029 A1 | 1/1987 |
| WO | WO 93/20784 A1 | 10/1993 |
| WO | WO 94/05257 A1 | 3/1994 |
| WO | WO 95/26734 A1 | 10/1995 |
| WO | WO 95/28984 A1 | 11/1995 |
| WO | WO 96/03978 A1 | 2/1996 |
| WO | WO 96/36377 A1 | 11/1996 |
| WO | WO 98/24504 A2 | 6/1998 |
| WO | WO 98/24504 A3 | 8/1998 |
| WO | WO 99/07418 A2 | 2/1999 |
| WO | WO 99/11244 A1 | 3/1999 |
| WO | WO 99/07418 A3 | 6/1999 |
| WO | WO 99/33853 A2 | 7/1999 |
| WO | WO 99/33853 A3 | 9/1999 |
| WO | WO 99/45920 A2 | 9/1999 |
| WO | WO 99/45920 A3 | 10/1999 |
| WO | WO 99/65548 A1 | 12/1999 |
| WO | WO 00/07530 A2 | 2/2000 |
| WO | WO 00/07565 A2 | 2/2000 |
| WO | WO 00/07530 A3 | 3/2000 |
| WO | WO 00/07565 A3 | 5/2000 |
| WO | WO 00/07530 A8 | 8/2000 |
| WO | WO 00/74752 A1 | 12/2000 |
| WO | WO 01/10482 A1 | 2/2001 |
| WO | WO 02/07658 A1 | 1/2002 |
| WO | WO 01/10482 A9 | 9/2002 |
| WO | WO 03/006098 A1 | 1/2003 |
| WO | WO 2004/030729 A1 | 4/2004 |
| WO | WO 2005/027578 A1 | 3/2005 |
| WO | WO 2006/037969 A1 | 4/2006 |
| WO | WO 2006/050008 A1 | 5/2006 |
| WO | WO 2006/067480 A1 | 6/2006 |
| WO | WO 2006/068921 A2 | 6/2006 |
| WO | WO 2006/108026 A2 | 10/2006 |
| WO | WO 2008/105954 A2 | 9/2008 |
| WO | WO 2008/108886 A2 | 9/2008 |
| WO | WO 2008/108886 A3 | 11/2008 |
| WO | WO 2008/105954 A3 | 3/2009 |
| WO | WO 2006/068921 A3 | 4/2009 |

OTHER PUBLICATIONS

Sidorenko, et al., "Method of Placing Irrigation System into Tenon's Space," Abstract of Russian Patent No. RU2123314, Patent Publication date Dec. 20, 1998, 1 pg.

Nesterov, et al., "A New Method for Posterior Sub-Tenon's Drug Administration," Ophthalmic Surgery, vol. 24, No. 1, Jan. 1993, 3 pgs.

Smith, et al., Uveitis: A Clinical Approach to Diagnosis and Management (Second Edition), Copyright 1989, 28 pages.

Roman, et al., "Sub-Tenon's Anaesthesia: An Efficient and Safe Technique," British Journal of Ophthalmology, 81:8, 1997, 4 pages.

P.A. Guise, "Single Quadrant Sub-Tenon's Block: Evaluation of a New Local Anaesthetic Technique for Eye Surgery," Anaesthesia and Intens Care, 24:241-244, Apr. 1996, 4 pages.

Stevens, "Curved, Sub-Tenon Cannula for Local Anesthesia," Ophthalmic Surgery, 24: 121-122, Feb. 1993, 2 pages.

Muthusamy, et al., "A Modified Sub-Tenon's Cannula for Local Anesthesia," Asia-Pacific Journal of Ophthalmology, vol. 8, No. 3, Jul. 1996, 6 pages.

Katena Products, Inc., Katena Eye Instruments, Catalog Supplement, 1997, 3 pages.

Hansen, et al., "Ocular Anesthesia for Cataract Surgery: A Direct Sub-Tenon's Approach," Ophthalmic Surgery, vol. 21, No. 10, Oct. 1990, 4 pages.

Mein, et al., "Local Anesthesia for Vitreoretinal Surgery," Retina, 10:47-49, 1990, 3 pages.

Freeman, et al., "Echocardiograph Localization of Corticosteriod after Periocular Injection," American Journal of Ophthalmology, vol. 100, No. 10, Oct. 1993, 5 pages.

Buys, et al., "Prospective Study of Sub-Tenon's versus Retrobulbar Anesthesia for Inpatient and Day-Surgery Trabeculectomy," Ophthalmology, vol. 100, No. 10, Oct. 1993, 5 pages.

Dialog File 266-FIDRIP database record; Identifying No. 122098; "Implantation of a Sub-Tenon Drug Delivery Device Loaded with a Test Article in Rabbits and Distribution of the Test Article in Ocular Tissues;" Compiled and distributed by NTIS, Jun. 3, 1999, 1 page.

Mendez, Internet printouts for Eagle Laboratories Tri-Port Sub-Tenon 100-19, 100-19c, 100-21C cannulas, Oct. 26, 1992, 1 page.

Uthoff, Internet printouts for Moria, Inc. 111275 G (25G Retrobulbar Curved, 121278 (19G Sub-Tenon) cannulas, Dec. 9, 1996, 1 page.

Ultra™ 2800 Positive Displacement; 2004; EFD, Inc. Brochure XP 1104 vol. 11.10; 2 pages.

Parker, "Your Resource for Motion and Fluid Control Components, Systems and Solutions," 8 pages.

Sanchez, Robert, "Multiple Chamber Drug Delivery," U.S. Appl. No. 12/536,527, filed Aug. 9, 2006, 30 pages.

* cited by examiner

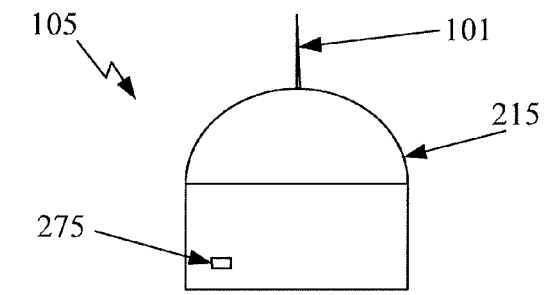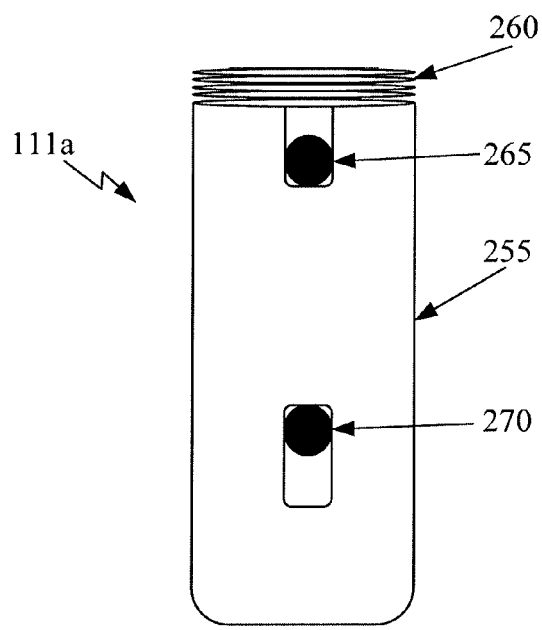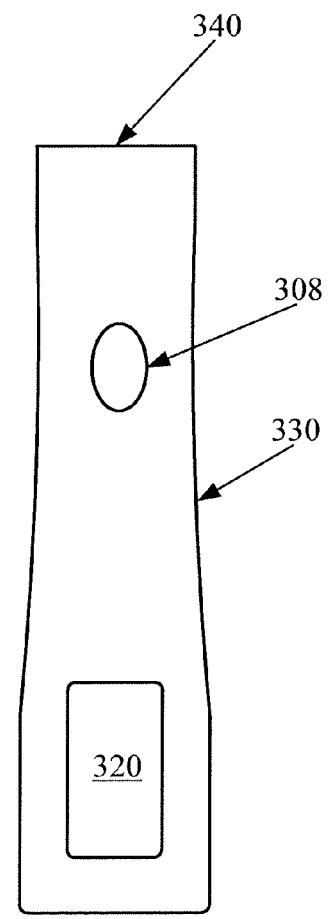
FIG. 2
FIG. 3

US 8,372,036 B2

MULTI-LAYER HEAT ASSEMBLY FOR A DRUG DELIVERY DEVICE

PRIORITY

This application claims the benefit of priority of U.S. Provisional Patent Application Ser. No. 61/175,813 titled "Multi-layer Heat Assembly for a Drug Delivery Device", filed on May 6, 2009, whose inventor is Cesario Dos Santos, which is hereby incorporated by reference in its entirety as though fully and completely set forth herein.

This application also claims the benefit of priority of U.S. Provisional Patent Application Ser. No. 61/289,467 titled "Phase Transition Drug Delivery System", filed on Dec. 23, 2009, whose inventors are Cesario Dos Santos and Michael Gelvin, which is hereby incorporated by reference in its entirety as though fully and completely set forth herein.

FIELD OF THE INVENTION

The present invention generally pertains to temperature control devices. More particularly, but not by way of limitation, the present invention pertains to temperature control devices for ophthalmic injections.

DESCRIPTION OF THE RELATED ART

Many diseases of the eye can be treated by injecting a drug into an eye. Injecting a drug into the eye may require control of both the volume and the temperature of the drug to avoid complications. For example, volume control may be important to avoid excessive pressure build-up in the eye. In addition, temperature of the drug may be adjusted to control, for example, a form of the drug (e.g., heated to a liquid for insertion) and/or rate of absorption of the drug into the eye.

SUMMARY OF THE INVENTION

In various embodiments, an ophthalmic injection device may include a dispensing chamber, a first thermal sensor coupled to the dispensing chamber, a temperature control layer coupled to the dispensing chamber, a second thermal sensor coupled to the dispensing chamber, and a first processing device. The first processing device may be configured to receive temperature information from the first and second thermal sensors and control the temperature control layer using the received temperature information.

In some embodiments, the ophthalmic injection device may include a second processing device coupled to the first thermal sensor. The second processing device may be configured to send temperature information from the first thermal sensor (e.g., in digital form) to the first processing device (which may be located, for example, in the dispensing assembly of the ophthalmic injection device). In some embodiments, the first processing device may receive temperature information directly from the second thermal sensor (e.g., in analog form) and may compare the temperature information from the first thermal sensor (received from the first processing device) and the second thermal sensor to detect temperature offsets between the two sensors.

BRIEF DESCRIPTION OF THE DRAWINGS

For a more complete understanding of the present invention, reference is made to the following description taken in conjunction with the accompanying drawings in which:

FIG. 2 is one view of an ophthalmic injection device including a disposable tip segment and a dispensing assembly according to an embodiment;

FIG. 3 is another embodiment of a dispensing assembly;

It is to be understood that both the foregoing general description and the following detailed description are exemplary and explanatory only and are intended to provide a further explanation of the present invention as claimed.

DETAILED DESCRIPTION OF THE EMBODIMENTS

Incorporation by Reference

U.S. patent Application Publication entitled "Dispensing Assembly For Ophthalmic Injection Device," Publication No. 20070270744, Ser. No. 11/832,364, by Bruno Dacquay, Cesario Dos Santos, James Foster, Casey Lind, Raffi Pinedjian, and Robert Sanchez filed Aug. 1, 2007 is hereby incorporated by reference in its entirety as though fully and completely set forth herein.

Figure 1:
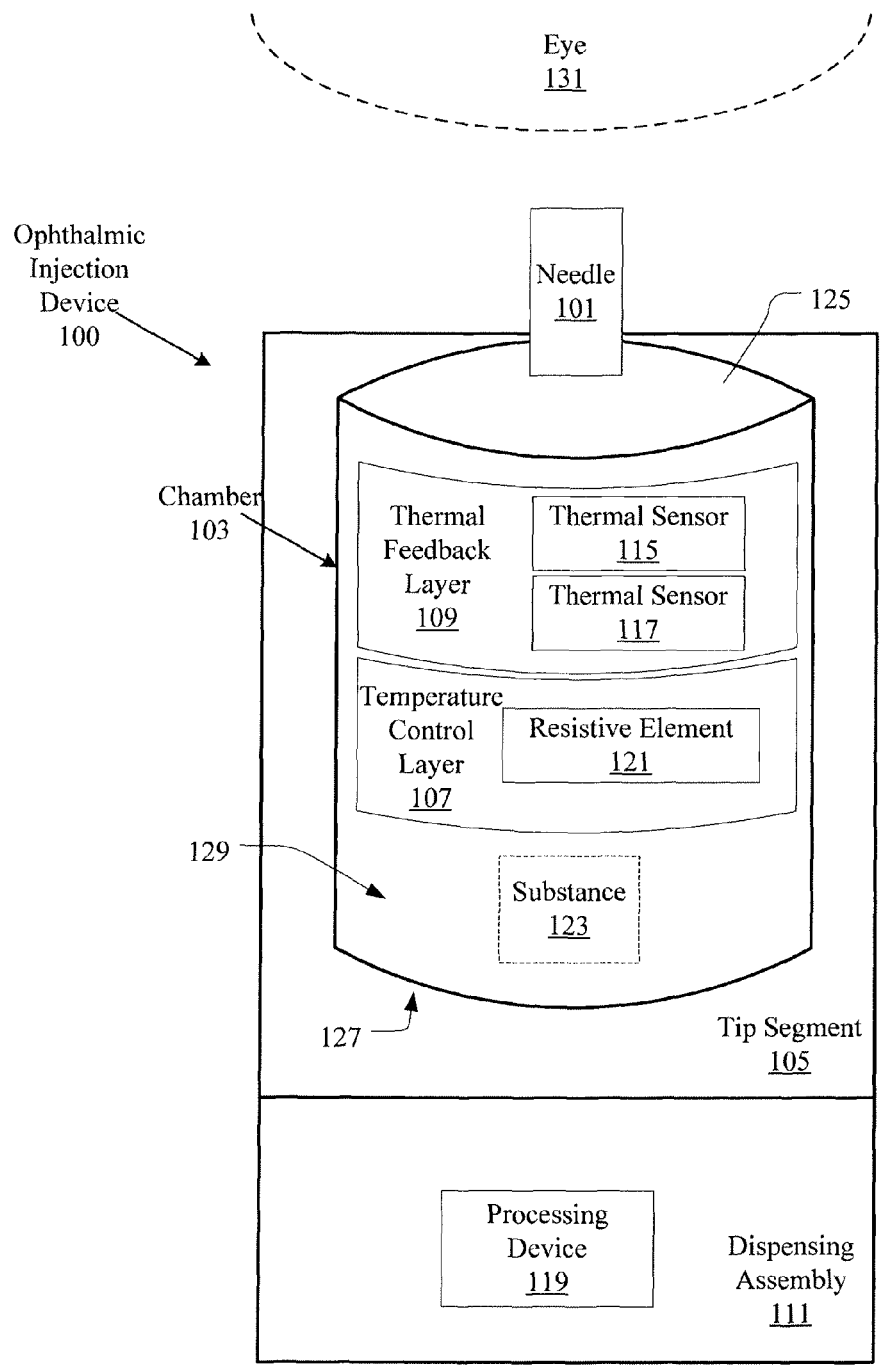
FIG. 1 illustrates a block diagram of an ophthalmic injection device including a dispensing assembly coupled to a tip segment, according to an embodiment.

FIG. 1 illustrates a block diagram of an ophthalmic injection device 100 including a dispensing assembly 111 coupled to a tip segment 105. In some embodiments, the tip segment 105 may include a dispensing chamber 103 coupled to a thermal feedback layer 109 and a temperature control layer 107. The thermal feedback layer 109 may include one or more thermal sensors (e.g., thermal sensors 115 and 117) that provide temperature information to a processing device 119 (which may be located in the dispensing assembly 111 or the tip segment 105). In some embodiments, the thermal sensors may include a thermistor, a thermocouple, etc. and the temperature information may include, for example, a temperature, a temperature gradient, or a change in voltage, current, resistance, etc. that is indicative of a temperature, change in temperature (e.g., a change in resistance on a thermistor), etc. "Dispensing assembly 111" is used herein to generally refer to the dispensing assembly of the ophthalmic injection device 100 and embodiments of the dispensing assembly are denoted herein by letter indicators (e.g., dispensing assembly 111a in FIG. 2, dispensing assembly 111b in FIG. 3, etc).

In some embodiments, first processing device 119 (and/or other processing devices such as second processing device 901 shown in FIGS. 9a, 9c, 10a, 10c, and 11a) may be programmable to function to control various components of the ophthalmic injection device 100. For example, the first processing device 119 may use temperature information received from the thermal sensors to regulate the temperature control layer 107 (e.g., first processing device 119 may interface with the temperature control layer 107 to activate/deactivate a resistive element 121 on the temperature control layer 107, increase/decrease a heat output of the resistive element 121, etc). In some embodiments, the resistive element 121 of the temperature control layer 107 may include resistive traces embedded in a flexible insulation layer that convert electrical current into heat or use electrical current to move heat. For example, the resistive traces may include resistive heater traces embedded in Kapton™ and wrapped around the dispensing chamber 103 to heat the dispensing chamber 103 and a substance 123 in the dispensing chamber 103. As another example, the resistive element 121 may include a thermoelectric heat pump with a cool side of the heat pump placed in contact with the dispensing chamber 103 to cool the dispensing chamber 103 and a substance 123 in the dispensing chamber 103. Other resistive elements 121 are also contemplated. Once heated or cooled, the substance 123 in the chamber 103 may be injected into an eye 131 through the needle 101.

As seen in FIG. 1, the dispensing chamber 103 may be substantially cylindrical with a first end face 125, a second end face 127, and a side face 129 coupling the first end face 125 and the second end face 127. The thermal feedback layer 109 and temperature control layer 107 may be at least partially wrapped around the side face 129 and/or each other to apply or remove heat through the side face 129 and detect temperature information associated with a temperature of a substance 123 in the chamber 103. For example, the thermal feedback layer 109 and temperature control layer 107 may cover a percentage of the area of the side face 129 (e.g., >33% covered, >50% covered, >75% covered, etc). In some embodiments, the thermal feedback layer 109 and temperature control layer 107 may be wrapped completely around (i.e., 360 degrees around) the side face 129 and/or may overlap itself.

FIG. 2 is an embodiment of an ophthalmic injection device 100 including a disposable tip segment 105 and dispensing assembly 111a. The tip segment 105 may include a needle 101, a housing 215, and a light 275. While tip segment 105 is described throughout as "disposable", in some embodiments, tip segment 105 may be used repeatedly. The dispensing assembly 111a may include a housing 255, a switch 270, a lock mechanism 265, and a threaded portion 260. In some embodiments, tip segment 105 may be removably coupled to dispensing assembly 111a (e.g., through a threaded portion on an interior surface of housing 215 that screws onto the threaded portion 260 of dispensing assembly 111a). In addition, lock mechanism 265 may secure tip housing 215 to dispensing assembly 111a. Other coupling mechanisms for the tip segment 105 and the dispensing assembly 111a are also contemplated (e.g., adhesive, snaps, or a unitary housing for the tip segment 105 and dispensing assembly 111a). Needle 101 may be configured to deliver a substance 123 from the dispensing chamber 103, such as a drug, into an eye 131. Needle 101 may be configured with thermal characteristics that are conducive to drug delivery. For example, needle 101 may be relatively short (e.g., on the order of several millimeters) in length (for thermal purposes) to facilitate proper delivery of a temperature controlled drug. In some embodiments, switch 270 may be used to activate the system or to turn on a temperature control layer 107.

FIG. 3 illustrates another embodiment of dispensing assembly 111b. Dispensing assembly 111b may include a button 308, a display 320, and a housing 330. Disposable tip segment 105 may attach to end 340 of dispensing assembly 111b. In some embodiments, button 308 may activate a temperature control layer 107 or initiate actuation of a plunger.

Figure 4:
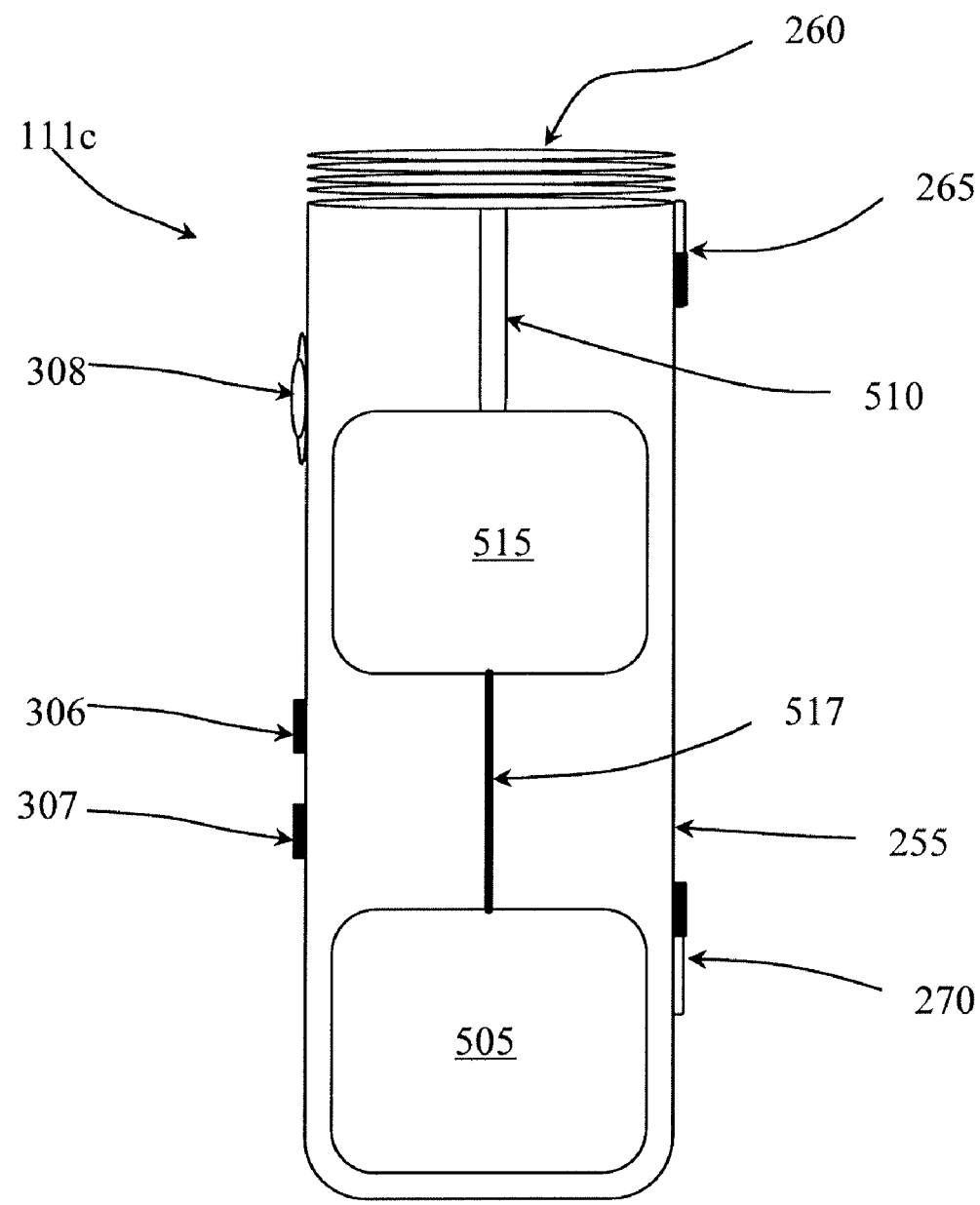
FIG. 4 is a cross section view of another embodiment of a dispensing assembly.

FIG. 4 illustrates a cross section view of an embodiment of dispensing assembly 111c. As seen in FIG. 4, power source 505, interface 517, actuator 515, and actuator shaft 510 may be located in housing 255. The top part of housing 255 may have a threaded portion 260. Lock mechanism 265, switch 270, button 308, and indicators 306, 307 may all be located on housing 255. Power source 505 may provide power to tip segment 105 connected to dispensing assembly 111c. For example, power source 505 may provide power to a temperature control layer 107 and/or thermal feedback layer 109 located in the tip segment 105.

In some embodiments, actuator shaft 510 may be connected to and driven by actuator 515. Actuator 515 may be a stepper motor or other type of motor that is capable of moving actuator shaft 510 precise distances. In some embodiments, actuator shaft 510 may be connected via a mechanical linkage to tip segment 105 that delivers a drug into an eye 131. Actuator 515 may be a stepper motor that may precisely move shaft 510 to deliver a precise quantity of drug into the eye 131. Actuator 515 may be secured to an interior surface of housing 255 by, for example, tabs that engage the outer surface of actuator 515.

Figure 5:
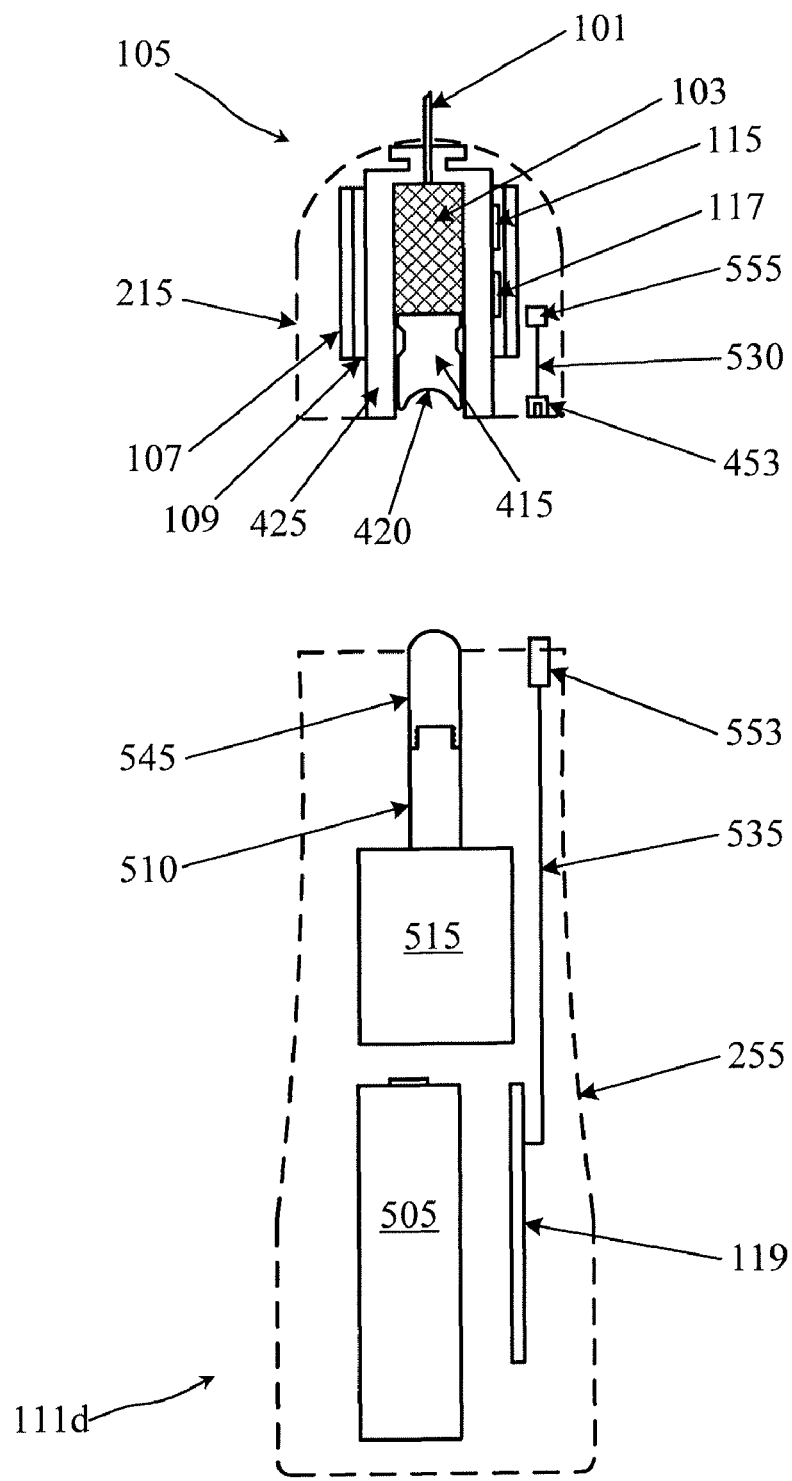
FIG. 5 is a cross section view of a disposable tip segment and a dispensing assembly, according to an embodiment.

FIG. 5 illustrates a cross section view of a disposable tip segment 105 interfacing with a dispensing assembly 111d, according to an embodiment. In the embodiment shown in FIG. 5, tip segment 105 may include assembly 555, temperature control layer 107, thermal feedback layer 109 (with thermal sensors 115 and 117), plunger interface 420, plunger 415, dispensing chamber housing 425, tip segment housing 215, needle 101, dispensing chamber 103, interface 530, and tip interface connector 453. While thermal feedback layer 109 is shown under the temperature control layer 107, this may be reversed (e.g., with the temperature control layer 107 under the thermal feedback layer 109). In some embodiments, the thermal feedback layer 109 and the temperature control layer 107 may be comprised in a single layer. In some embodiments, dispensing chamber housing 425 may have a recessed portion that receives the temperature control layer 107 and/or the thermal feedback layer 109. Dispensing assembly 111d may include mechanical linkage interface 545, actuator shaft 510, actuator 515, power source 505, first processing device 119, dispensing assembly housing 255, interface 535, and dispensing assembly interface connector 553.

In some embodiments, assembly 555 may include a fuse 601 that is blown when a heat button is activated or according to instructions from a first processing device 119 or second processing device 901 after disposable tip segment 105 is used (e.g., to prevent reuse of disposable tip segment 105). For example, as seen in FIGS. 6c and 7b, the fuse 601 may be in parallel with the heating element 121 (which may not necessarily be include in assembly 555). Other configurations of 555 are also contemplated. For example, assembly 555 may include a memory device that stores information about the type of disposable tip segment 105, dosage information, temperature information, plunger movement information, or any other type of information that identifies a characteristic of disposable tip segment 105 or a manner in which disposable tip segment 105 is operated. For example, assembly 555 may include a hard-wired memory device, like an NAND (Not And electronic logic gate) flash IC (integrated circuit), an RFID (Radio Frequency Identification) tag, a hard-wired wired circuit that can store a representation of data (e.g., a series of fuses and resistors connected in parallel), or other type of device.

In some embodiments, plunger interface 420 may be located on one end of plunger 415 in tip segment 105. The other end of plunger 415 may form one end of dispensing chamber 103. Plunger 415 may slide within dispensing chamber 103. The outer surface of plunger 415 may be fluidly sealed to the inner surface of dispensing chamber housing 425. Dispensing chamber housing 425 may surround the dispensing chamber 103 (both of which may have a cylindrical shape). In some embodiments, needle 101 may be fluidly coupled to dispensing chamber 103. A substance 123 (such as a drug) contained in dispensing chamber 103 may pass through needle 101 and into an eye 131. Temperature control layer 107 may at least partially surround dispensing chamber housing 425 and may be connected to tip interface connector 453 through interface 530. Temperature control layer 107 may include a resistive element 121 configured to heat or cool dispensing chamber housing 425 and any substance 123 contained in dispensing chamber 103 (which may be made of a thermally conductive material such as copper, steel, etc). Other materials are also contemplated.

The components of tip segment 105, including dispensing chamber housing 425, temperature control layer 107, and plunger 415 may be at least partially enclosed by tip segment housing 215. In some embodiments, plunger 415 may be sealed to the interior surface of dispensing chamber housing 425. This seal may prevent contamination of a substance 123 contained in dispensing chamber 103. This seal may be located at any point on plunger 415 or dispensing chamber housing 425.

In some embodiments, first processing device 119 and actuator 515 may be connected by an interface to allow first processing device 119 to control the operation of actuator 515. In addition, an interface between power source 505 and first processing device 119 may allow first processing device 119 to control operation of power source 505 (which may supply power to the first processing device 119 and/or actuator 515). In such a case, first processing device 119 may control the charging and the discharging of power source 505 when power source 505 is a rechargeable battery.

In some embodiments, tip segment 105 may mate with or be attached to dispensing assembly 111. As seen in FIG. 5, plunger interface 420 may be located on a bottom surface of plunger 415 that mates with mechanical linkage interface 545 located near a top surface of dispensing assembly housing 255. In addition, tip interface connector 453 may connect with dispensing assembly interface connector 553. When tip segment 105 is connected to dispensing assembly 111 in this manner, actuator 515 and actuator shaft 510 may drive plunger 415 toward needle 101. A signal may pass between first processing device 119 and the thermal feedback layer 109 or temperature control layer 107 through interface 535, dispensing assembly interface connector 553, tip interface connector 453, and/or interface 530.

In operation, when tip segment 105 is connected to dispensing assembly 111, first processing device 119 may control operation of actuator 515. When actuator 515 is actuated, actuator shaft 510 may move toward needle 101. In turn, mechanical linkage interface 545, which may be mated with plunger interface 420, may move plunger 415 toward needle 101. A substance 123 located in dispensing chamber 103 may then be expelled through needle 101.

In some embodiments, first processing device 119 and/or second processing device 901 may control the operation of temperature control layer 107 based on temperature information received from the first and/or second thermal sensors. For example, temperature control layer 107 may include a heater and first processing device 119 may control the amount of current that is sent to the heater based on the received temperature information. In some embodiments, the temperature information may indicate an approximate temperature of the dispensing chamber 103 and the current may be adjusted to increase or decrease the temperature to a desired temperature. For example, as the current level increases, the temperature of a resistive element 121 in the heater may increase. In some embodiments, the current may be discontinued if the temperature information indicates a desired temperature has been obtained. Temperature control layer 107 may be in direct thermal contact with dispensing chamber housing 425 (or, for example, indirectly through thermal feedback layer 109). In some embodiments, temperature control layer 107 may heat and/or cool dispensing chamber housing 425. Since dispensing chamber housing 425 may be at least partially thermally conductive, heating or cooling dispensing chamber housing 425 may heat or cool a substance 123 (such as a drug to be delivered into an eye 131) located in dispensing chamber 103.

In some embodiments, first processing device 119 may use a feed back loop utilizing information from the thermal sensors to control the operation of temperature control layer 107. A control algorithm, such as a proportional integral derivative (PID) algorithm with temperature information used as at least one of the inputs, may be used to control the operation of temperature control layer 107. In some embodiments, temperature information may be transferred from thermal sensor 115 through interface 530, tip interface connector 453, dispensing assembly interface connector 553, and interface 535 back to first processing device 119.

In some embodiments, thermal sensor 115 may include a resistive device whose resistance varies with temperature for providing temperature information to use in controlling the operation of temperature control layer 107. Thermal sensor 115 may be located on or near dispensing chamber 103 and/or housing 425 to measure a temperature of or near dispensing chamber 103 and/or housing 425. In some embodiments, the temperature information detected by the thermal sensor 115 may correlate to a temperature of the substance 123 in dispensing chamber 103. Therefore, temperature information for the dispensing chamber 103 and/or housing 425 may be used to control a temperature control layer 107 to heat/cool the substance 123 located in dispensing chamber 103. If the thermal characteristics of dispensing chamber housing 425 and the substance 123 is known, the temperature of temperature control layer 107 may be controlled through the temperature control layer 107. Powering the resistive element of temperature control layer 107 for a specified period of time may result in a calculable change in the temperature of the substance 123 in dispensing chamber 103.

Figure 6A:
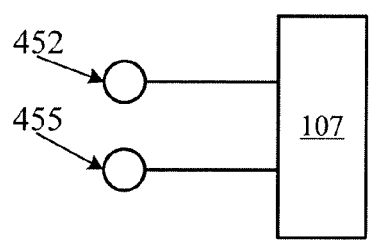
FIGS. 6a-c are schematic depictions of three different circuits that may be included in various embodiments.
Figure 6B:
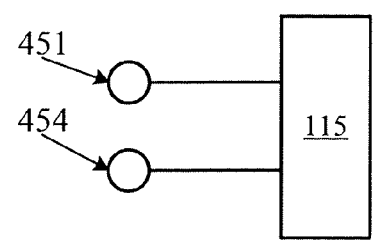
Figure 6C:
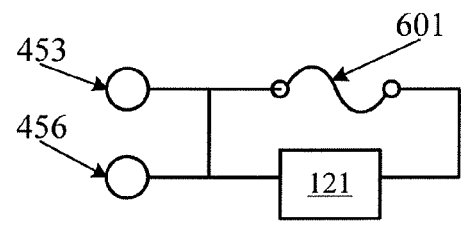

FIGS. 6a-6c are schematic depictions of three different circuit embodiments. FIG. 6a shows one of many different configurations for temperature control layer 107. In FIG. 6a, temperature control layer 107 is connected to connectors 452 and 455. Power and/or control signals may be provided to temperature control layer 107 through connectors 452 and

455. FIG. 6*b* shows one of many different configurations for thermal sensor 115. As seen in FIG. 6*b*, thermal sensor 115 may be connected to connectors 451 and 454. Signals may be received from thermal sensor 115 through connectors 451 and 454. Many other configurations of connectors 451, 452, 453, 454, 455, and 456 may be implemented. For example, while six connectors are shown, any number of connectors may be implemented. Further, different combinations of circuits may be contained in a tip segment 105.

Figure 7A:
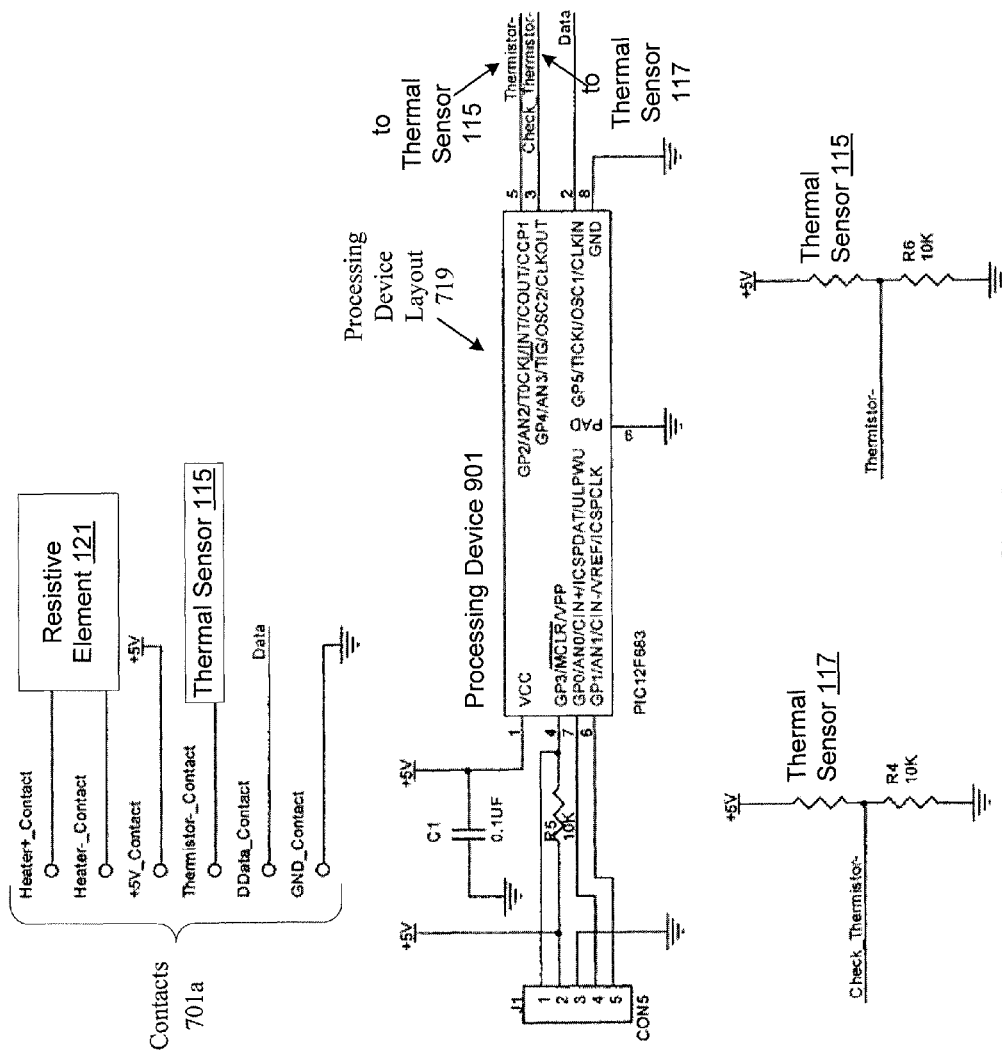
FIGS. 7a-7c illustrate circuit diagrams of an embodiment incorporating an additional thermal sensor.
Figure 7B:
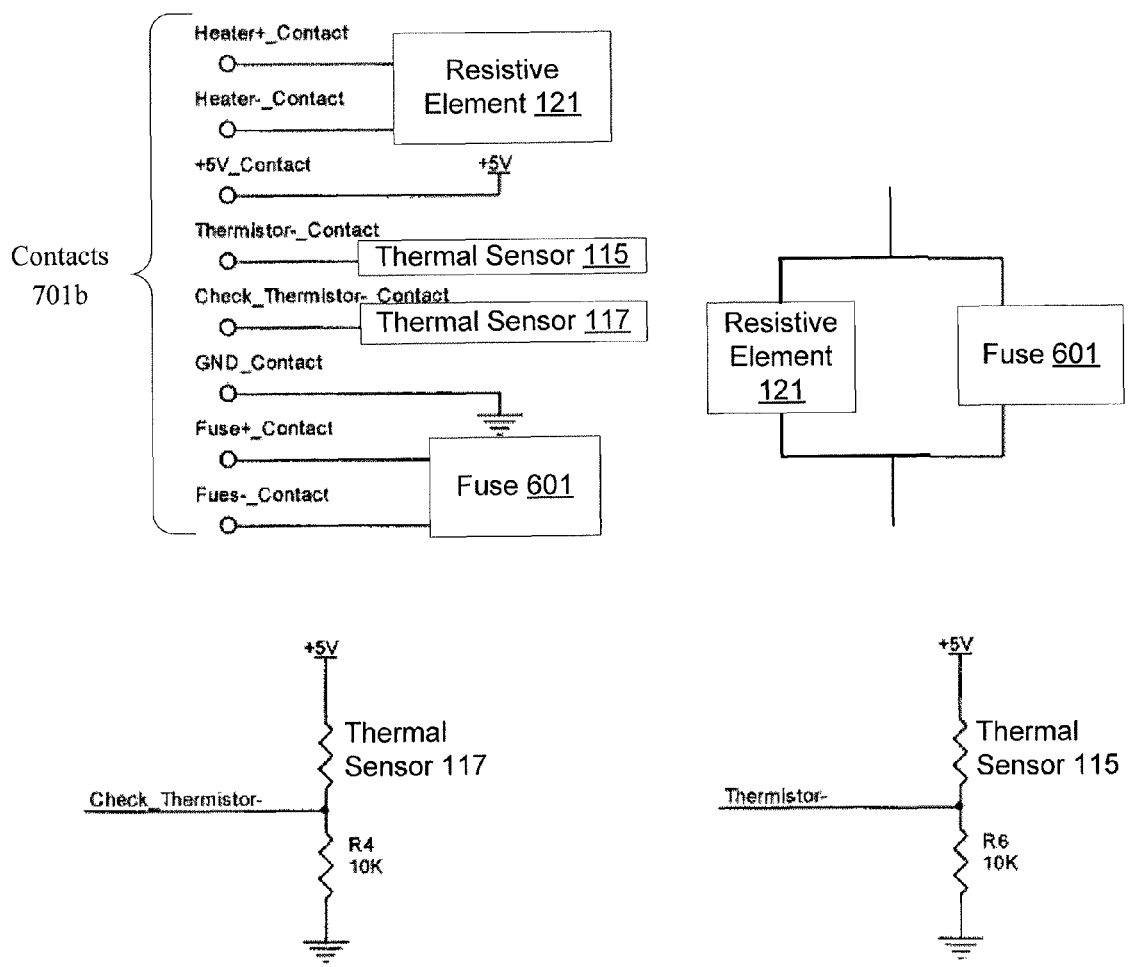
Figure 7C:
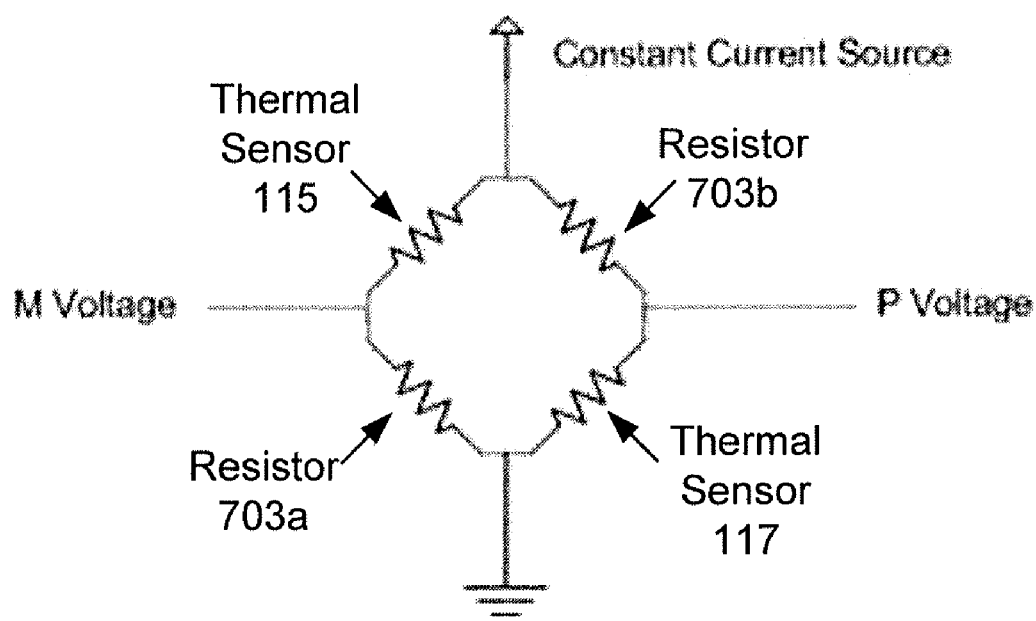

FIGS. 7*a*-7*c* illustrate circuit diagrams of an embodiment incorporating an additional thermal sensor (e.g., thermal sensor 117). In some embodiments, a feedback sensor (e.g., one or more thermal sensors) and/or a resistive element (e.g., on temperature control layer 107) may be coupled to the tip segment 105 through one or more contacts (e.g., contacts 701*a,b*). In some embodiments, the temperature control layer 107 and the thermal sensor 115 may be placed proximate to each other (e.g., may both be on the tip segment 105 and in thermal communication with each other). Additional thermal sensors (e.g., thermal sensor 117) may also be incorporated in the tip segment 105 and may be communicatively coupled to a processing device (e.g., processing device 119 or 901) controlling the temperature control layer 107. In some embodiments, thermal sensors 115,117 may include 20 k ohm thermistors (other thermistor sizes are also possible (e.g., 5 k ohm, 30 k ohm)). Processing device layout 719 in FIG. 7*a* illustrates an embodiment of a processing device layout for a processing device (such as processing device 119 which may be a PIC 12F683 processor). The additional thermal sensor 117 may add redundancy to the existing thermal sensor 115 and may provide additional sources of temperature information for use by the processing devices in controlling temperature control layer 107. The additional temperature information may be used by the processing devices to identify a faulty thermal sensor and/or other causes of impedance offsets (e.g., accumulated debris on a thermal sensor, an offset beta value, etc). As another example, a thermal sensor that includes a thermocouple with a poor solder joint may have an offset in the voltage between the thermocouple's junctions that may generate inaccurate thermal readings from the thermocouple. The additional thermal sensor 117 may reduce the effect of any in-series parasitic resistance on a voltage output from a junction of the first thermal sensor 115 (e.g., a thermistor) and a load resistance (e.g., the temperature control layer 107). The additional thermal sensor 117 may also eliminate single point failures in the thermistor sense circuit of the feedback layer 109. In some embodiments, a processing device may receive temperature information from the two or more thermal sensors 115/117 (e.g., separately as shown in FIG. 7*b* or may receive information on a respective difference (e.g., through sensed current/voltage from lines M Voltage and P Voltage which may be electrically coupled to the processor) between the two sensor readings as seen in FIG. 7*c*) and may determine if the temperature information from the thermal sensors 115/117 are within a predetermined tolerance. In some embodiments, the thermal sensors 115/117 may be placed in a bridge configuration (e.g., see FIG. 7*c*) with two or more resistors (e.g., resistors 703*a,b*). The output voltage of the bridge circuit may indicate a difference in thermal sensor readings. In some embodiments, the resistors 703*a,b* may be 3000 ohm resistors (in some embodiments, the values of the thermistors used for the thermal sensors 115/117 may approach 3000 ohms at the desired temperature of operation). Further, using a bridge may minimize effects from stray resistances in contacts by leveraging the larger resistances of the bridge. Other resistance values are also possible. In some embodiments, the predetermined tolerance may be +/−5 degrees Celsius. Other tolerances may also be used. If temperatures derived from the temperature information are not within the predetermined tolerance (e.g., if one temperature is indicated as 10 degrees higher than the other detected temperature), the processing device (such as processing device 119 or 901) may indicate to the user that there is an error (which may indicate the tip segment 105 needs to be replaced). In some embodiments, the processing device and/or user may terminate a procedure (e.g., if the error is detected during a surgery) until a replacement tip segment or handpiece is located.

Figure 8A:
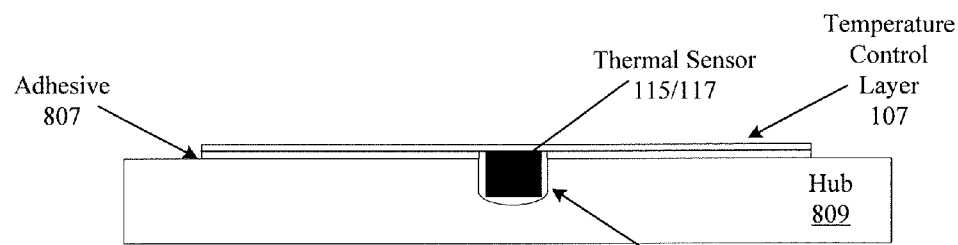
FIGS. 8a-8c illustrate configurations for thermally coupling a thermal sensor to a hub, according to various embodiments.
Figure 8B:
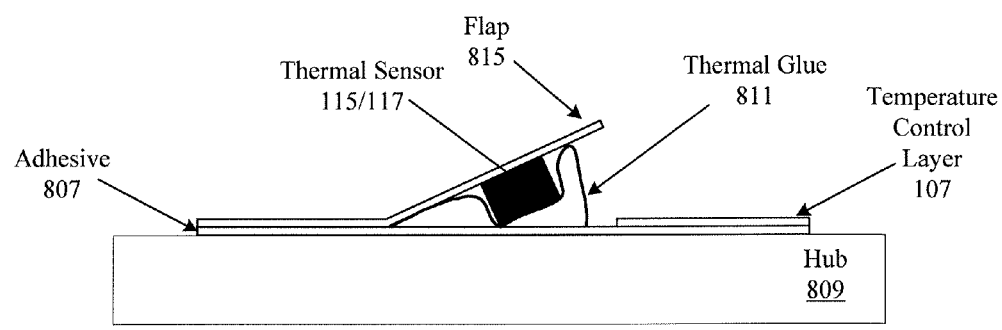
Figure 8C:
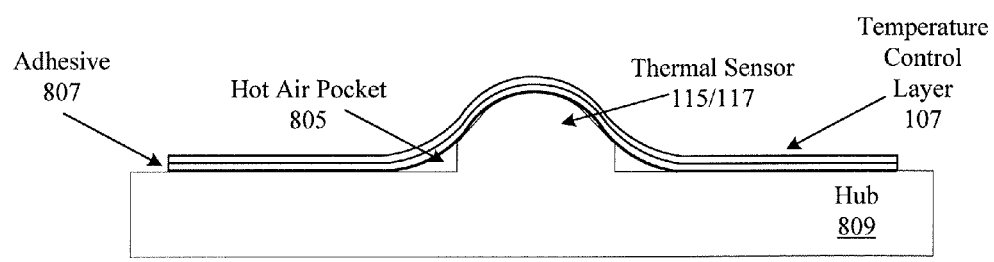

FIGS. 8*a*-8*c* illustrate configurations for thermally coupling a thermal sensor 115 or 117 (such as a thermistor) to a hub 809 (which may include, for example, a surface of the chamber 103 or dispensing chamber housing 425), according to various embodiments. As seen in FIG. 8*b*, a thermal sensor 115 (or thermal sensor 117) may be mounted onto a flap 815 on the same side as the object to whose temperature is being measured. The flap 815 may be held on one side/corner of the temperature control layer 107 and may give way (e.g., break away or tear) when the temperature control layer 107 is adhered to the hub's surface. In some embodiments, the thermal sensor 115/117 may be part of a thermal feedback layer 109 that includes sensory traces (e.g., copper, inconel, etc.) in an insulation material. For example, the one or more thermal sensors 115/117 may be traces insulated by Kapton™ (other insulation materials are also contemplated). In some embodiments, the thermal sensors 115/117 may be individual elements that are not in a layer configuration. Placing the thermal sensor 115/117 on the flap 815 and filling a gap between the thermal sensor 115/117 and the flap 815 with thermal glue 811 (a.k.a., thermal adhesive/thermal paste) and/or thermal grease may decrease an amount of surface area exposed to the colder ambient air within the ophthalmic injection device 100. The placement of the thermal sensor 115/117 and thermal glue 811 may also eliminate the insulating layer between the thermal sensor 115/117 and the chamber 103 to allow the thermal sensor 115/117 to provide a better approximation of the chamber temperature. In some embodiments, the thermal sensor 115/117 may be bonded directly to the hot hub 809. While a separate adhesive 807 is shown in FIG. 8*b* between the thermal sensor 115/117 and the hub 809, adhesive 807 may not be a separate element from thermal glue 811 (e.g., thermal glue 911 and/or thermal sensor 115/117 may extend to the hub 809). In some embodiments, adhesive 807 may be a separate/additional adhesive. In some embodiments, the adhesive 807 may be an insulating adhesive or may be a thermal adhesive. As seen in FIG. 8*a*, the thermal sensor 115/117 may be fitted into a recess 813 (e.g., a notched recess) in hub 809. As seen in FIG. 8*c*, the thermal sensor 115/117 may be placed between the insulation of the temperature control layer 107 and the hub 809. Placing the thermal sensor 115/117 in the recess 813 as seen in FIG. 8*a* may prevent the temperature control layer 107 from lifting and creating hot air pocket 805 (which may lead to a less accurate temperature reading by the thermal sensor). The temperature control layer 107 of FIG. 8*a* may need alignment between the thermal sensor 115/117 and the recess 813 during manufacturing to insure the thermal sensor 115/117 fits within the recess 813.

Figure 9A:
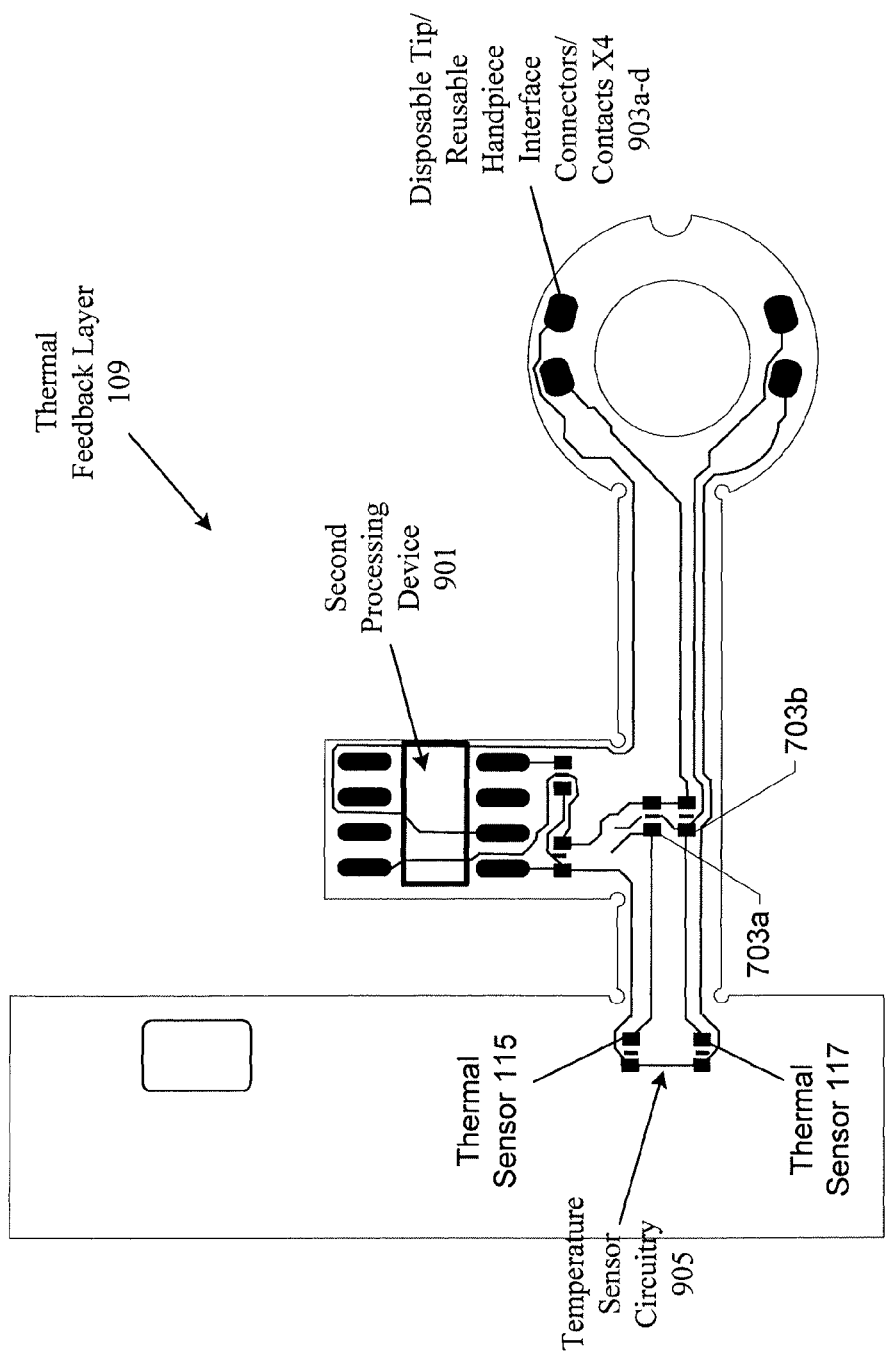
FIGS. 9a-9c illustrate an embodiment of a thermal feedback layer and a temperature control layer for a tip segment.
Figure 9B:
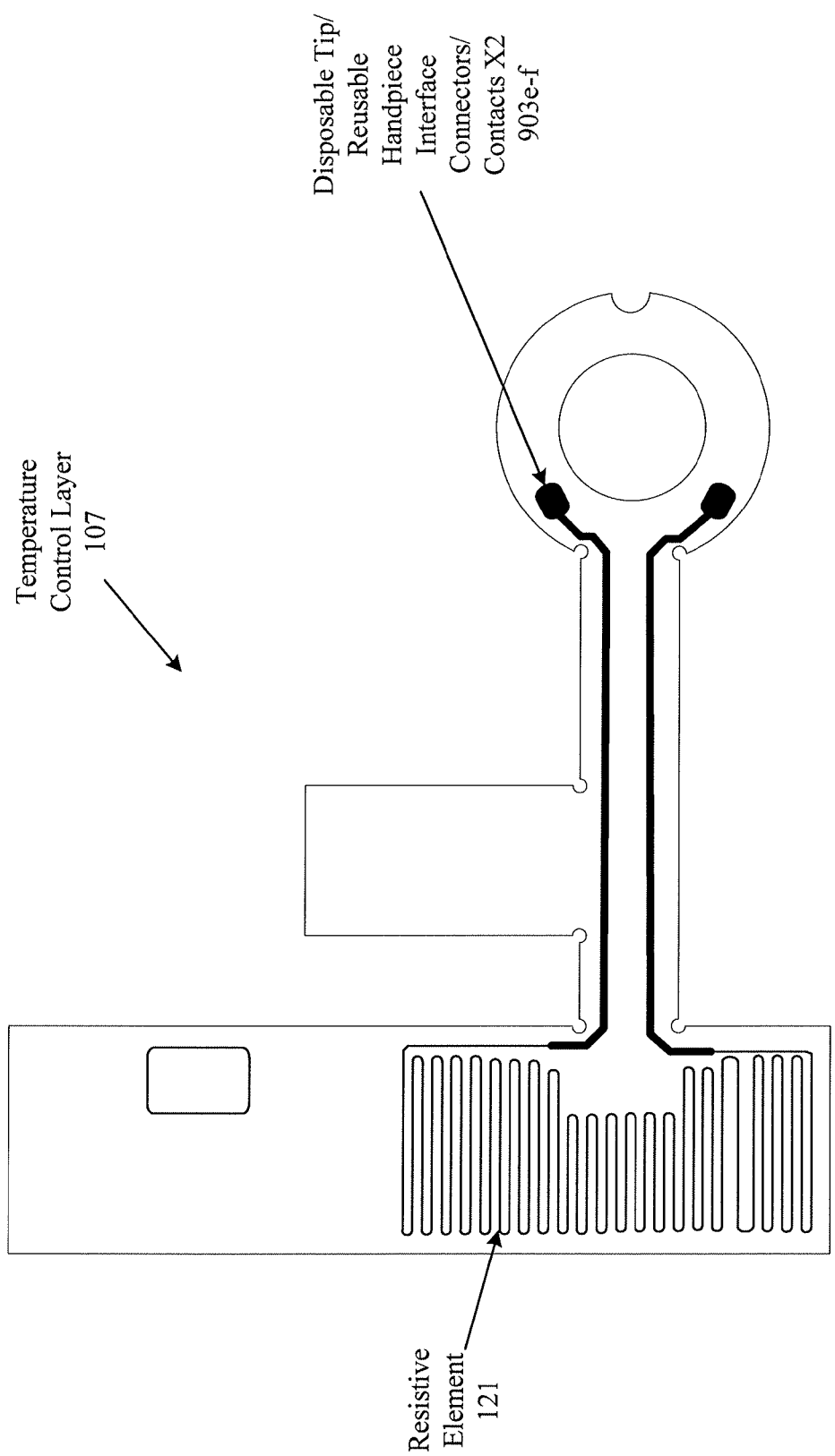
Figure 9C:
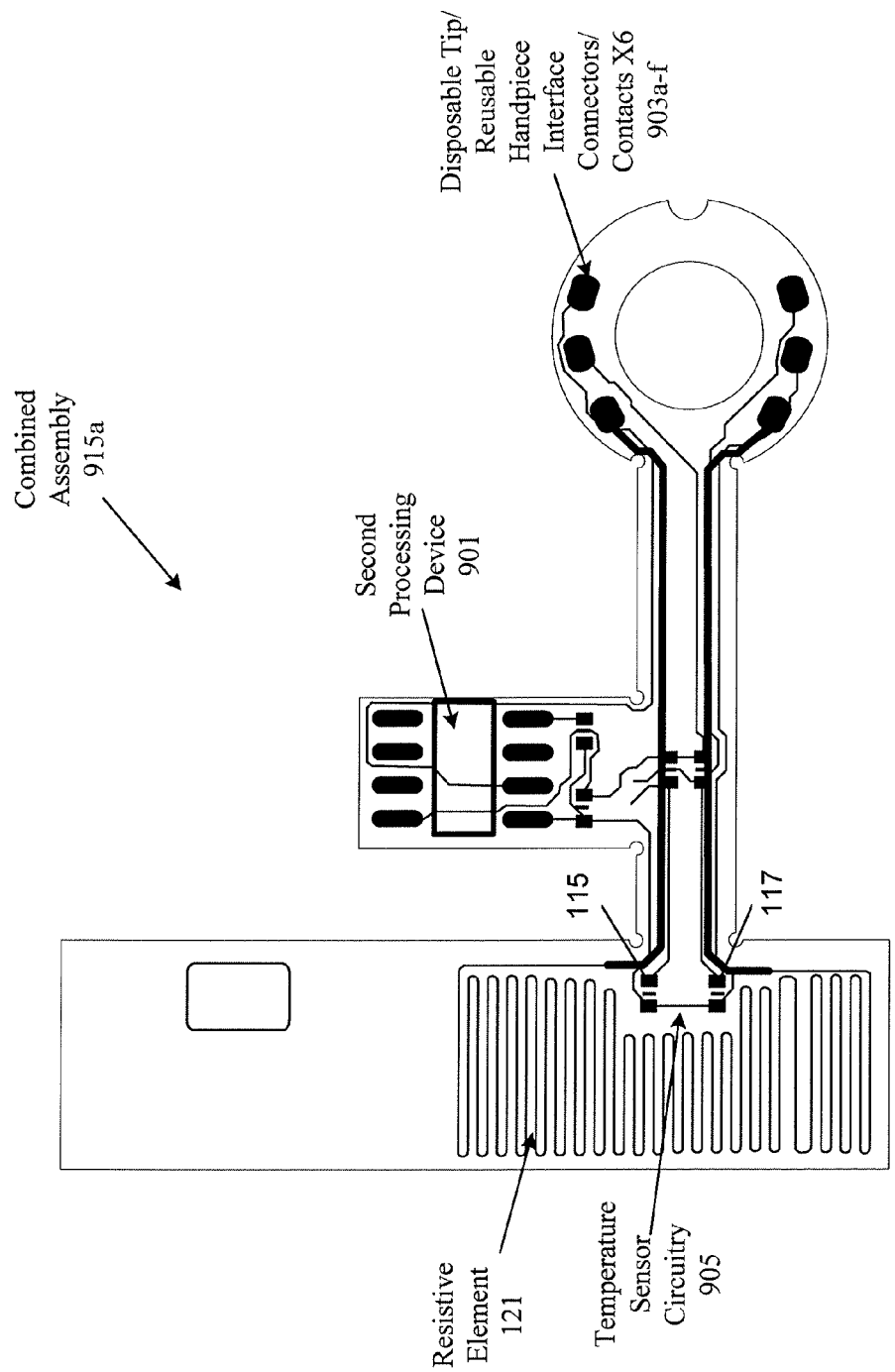

FIGS. 9*a*-9*c* illustrate an embodiment of a thermal feedback layer 109 and a temperature control layer 107 for a tip segment 105. In some embodiments, the thermal feedback layer 109 may include a closed loop thermal feedback circuit with temperature sensor circuitry 905 (which may include sensor traces for the thermal sensor 115 or 117). An embodiment of a form factor (i.e., the geometry/shape of the layer) for the thermal feedback layer 109 is shown in FIG. 9*a*. In some embodiments, the temperature control layer 107 may include a resistive element 121 (e.g., with multiple resistive traces that convert electrical current to heat through resistance). An embodiment of a form factor for the temperature control layer 107 is shown in FIG. 9*b*. In various embodiments, the temperature sensor circuitry 905 and resistive element 121 on the tip segment 105 may interface with the circuitry on the dispensing assembly through contact/connectors 903*a-f* (which may correlate to contacts 701*a* as seen in FIG. 7*a*).

In some embodiments, the sensor traces for a thermal sensor in the thermal feedback layer 109 (e.g., thermal sensor 115/117) may be made of copper, silver or gold. These materials may have low resistance and may be highly adherent to improve bondability of the thermal feedback layer 109 in an assembly (which may include the temperature control layer 107 and chamber 103). These materials may also reduce parasitic resistance caused by the sensor traces being smaller in width than the resistive traces on the temperature control layer 107. The reduced parasitic resistance may also reduce temperature offsets that may affect temperature information determined using the sensor traces on the thermal feedback layer 109. Other materials are also contemplated (e.g., inconel). In some embodiments, the thermal feedback layer 109 may include copper traces in a layer of Kapton™ and the temperature control layer 107 may include inconel traces in a layer of Kapton™. If the sensor traces are made of copper, silver, or gold instead of inconel, the thermal feedback layer 109 may have an improved bondability that may require less adhesive to bond the thermal feedback layer 109 to the temperature control layer 107 than if both the thermal feedback layer 109 and temperature control layer 107 included inconel traces.

In some embodiments, the thermal feedback layer 109 and the temperature control layer 107 may be manufactured as two separate layers that may then be bonded together to form a combined assembly 915*a* (see FIG. 9*c*). The combined assembly 915*a* may then be wrapped around the dispensing chamber 103 or dispensing chamber housing 425. For example, the thermal feedback layer 109 and the temperature control layer 107 may be bonded to each other (e.g., through a thermal adhesive) and the combined assembly 915*a* may be wrapped around and bonded to the dispensing chamber 103. In some embodiments, the thermal feedback layer 109 and the temperature control layer 107 may be separately wrapped around the dispensing chamber 103 or dispensing chamber housing 425. For example, the thermal feedback layer 109 or the temperature control layer 107 may be wrapped around and bonded to the dispensing chamber 103 and then the other of the thermal feedback layer 109 and the temperature control layer 107 may be wrapped around and bonded to the dispensing chamber 103 and/or previously wrapped layer. Thermal adhesive, solder, etc., may be used to bond the various layers to each other and/or the chamber 103 to thermally couple the layers to the chamber 103. In some embodiments, integrated circuits (e.g., forming a second processing device 901) may also be bonded to one or more of the thermal feedback layer 109 and the temperature control layer 107 (e.g., through solder). In some embodiments, the integrated circuits may not require adhesive in addition to the solder.

Figure 10A:
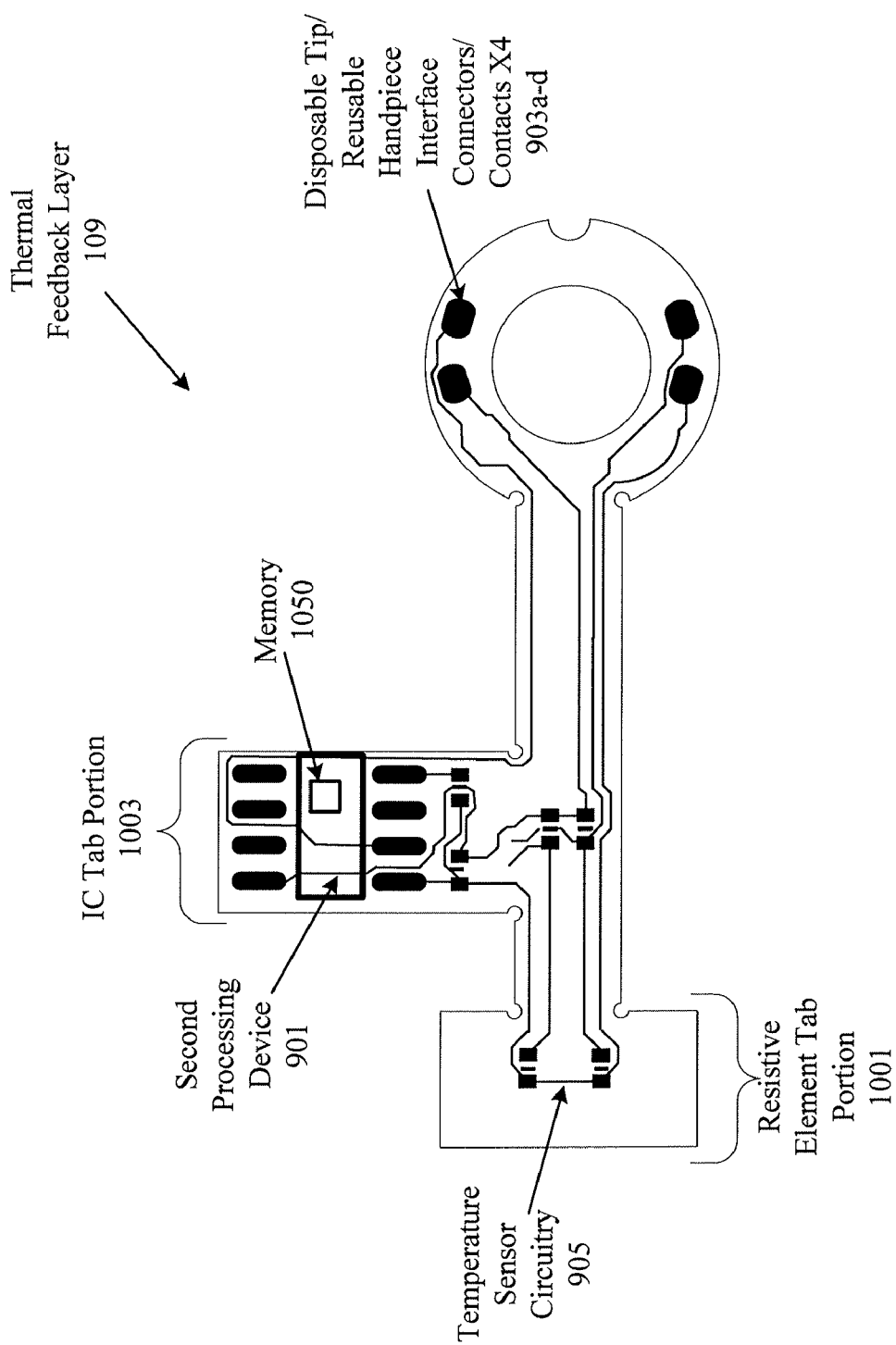
FIGS. 10a-c illustrates an embodiment utilizing different form factors for the thermal feedback layer and temperature control layer of the tip segment.
Figure 10B:
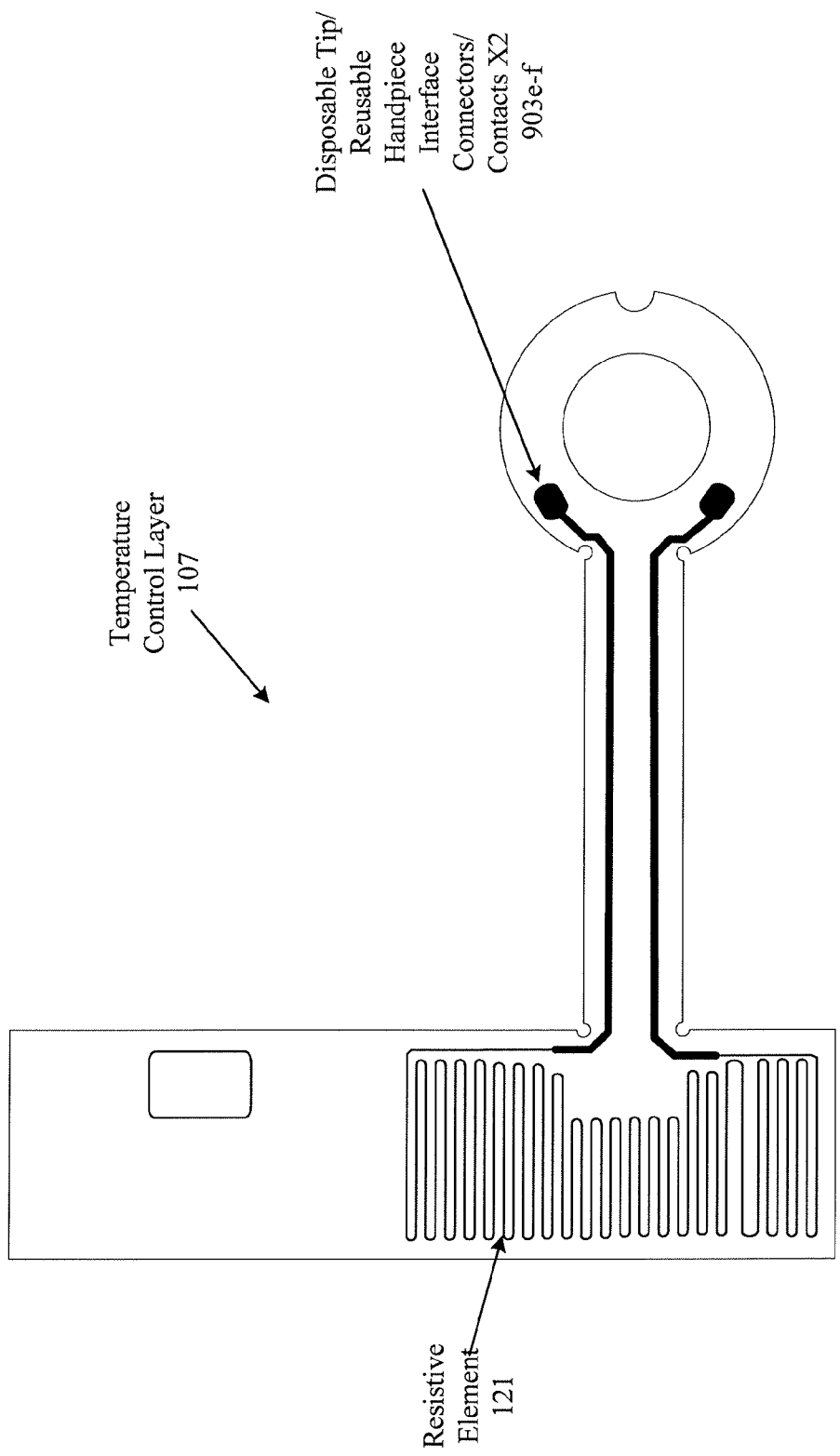
Figure 10C:
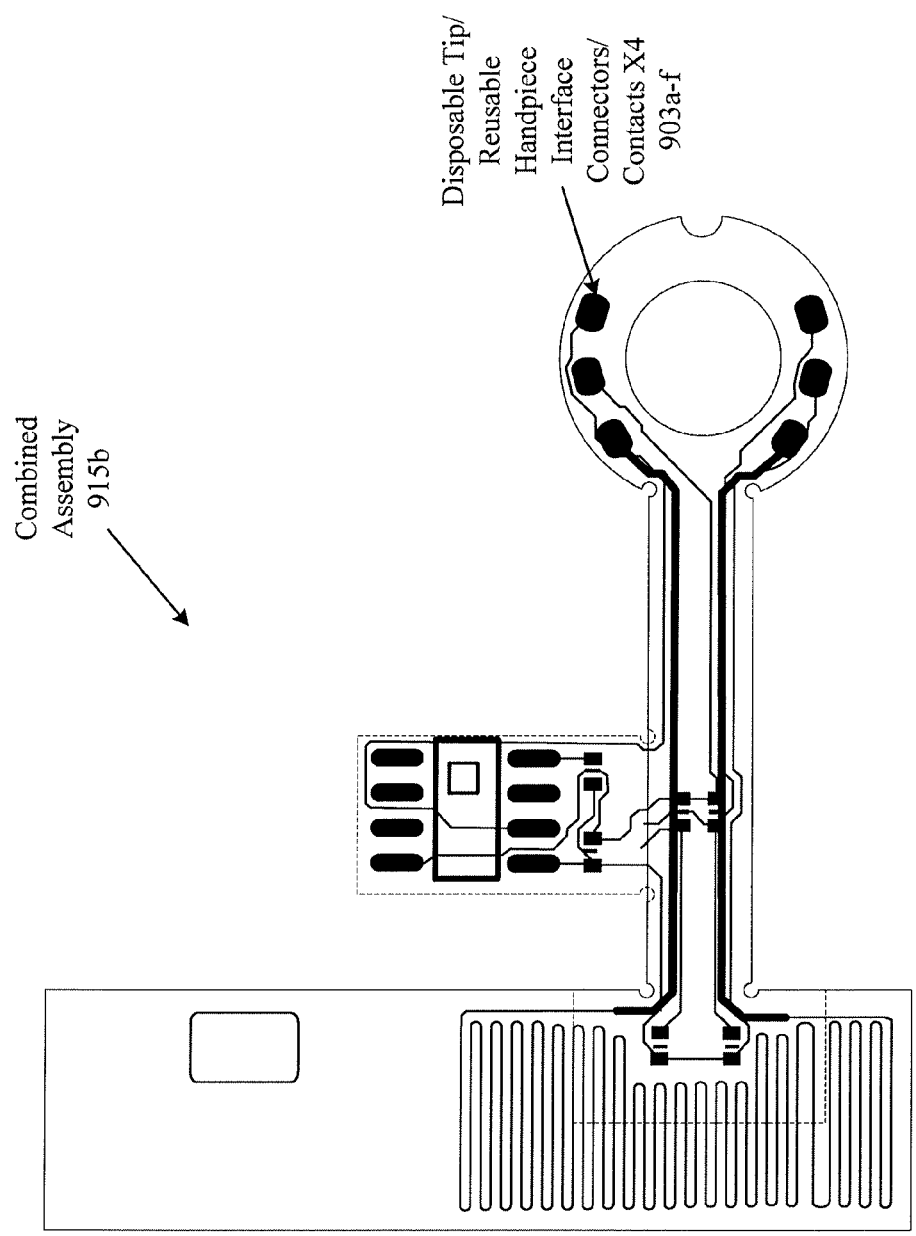

FIGS. 10*a-c* illustrate an embodiment with different form factors for the thermal feedback layer 109 and temperature control layer 107 of the tip segment 105. In some embodiments, the individual form factors of the thermal feedback layer 109 and/or temperature control layer 107 may be reduced to increase the flexibility of the layers 107/109 and/or combined assembly 915*b*. As seen in FIG. 10*a*, the thermal feedback layer 109 may include a form factor with a reduced resistive element tab portion 1001. In some embodiments, the temperature control layer (see FIG. 10*b*) may not include an IC tab portion 1003 in the temperature control layer form factor. These reduced form factors may increase the flexibility of each layer with respect to the other layers to improve bondability of the layers to each other and to the dispensing chamber and to improve the flexibility of the combined assembly 915*b* (improved flexibility versus if each layer had the same complete form factor). FIG. 10*c* illustrates an embodiment of combined assembly 915*b* with the thermal feedback layer 109 shown in dashed lines. In some embodiments, the reduced form factor layers may be easier to wrap around the chamber 103 or dispensing chamber housing 425 separately to form the combined assembly (which may improve manufacturability of the layers). Other form factors and form factor configurations are also contemplated. For example, other areas of the thermal feedback layer 109 and the temperature control layer 107 that do not have, for example, circuitry elements, may be removed or reduced. In addition, elements of the layers may be rearranged and non-used areas may be removed or reduced.

Figure 11A:
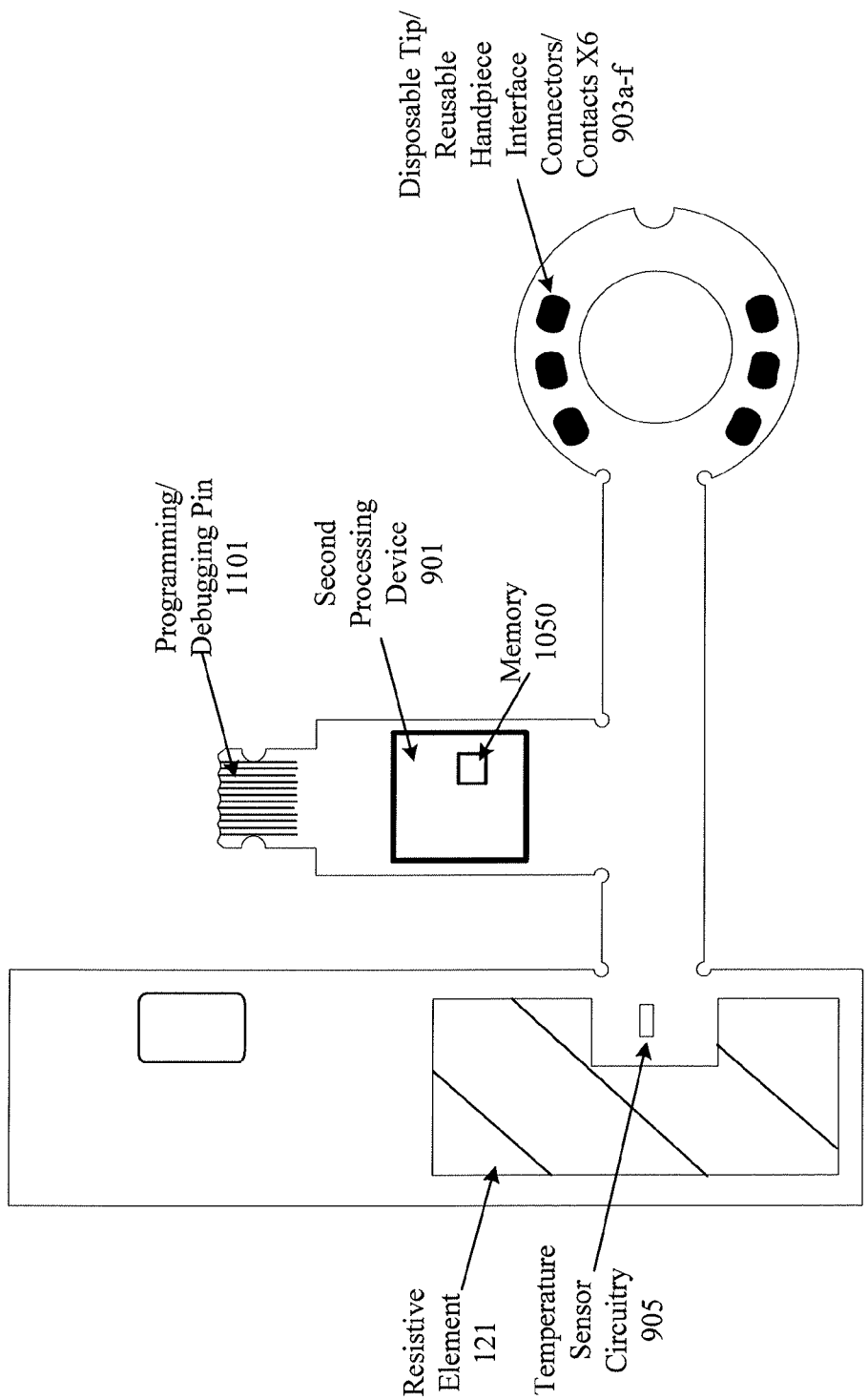
FIGS. 11a-b illustrate an embodiment with a second processing device to receive temperature information from a first thermal sensor.
Figure 11B:
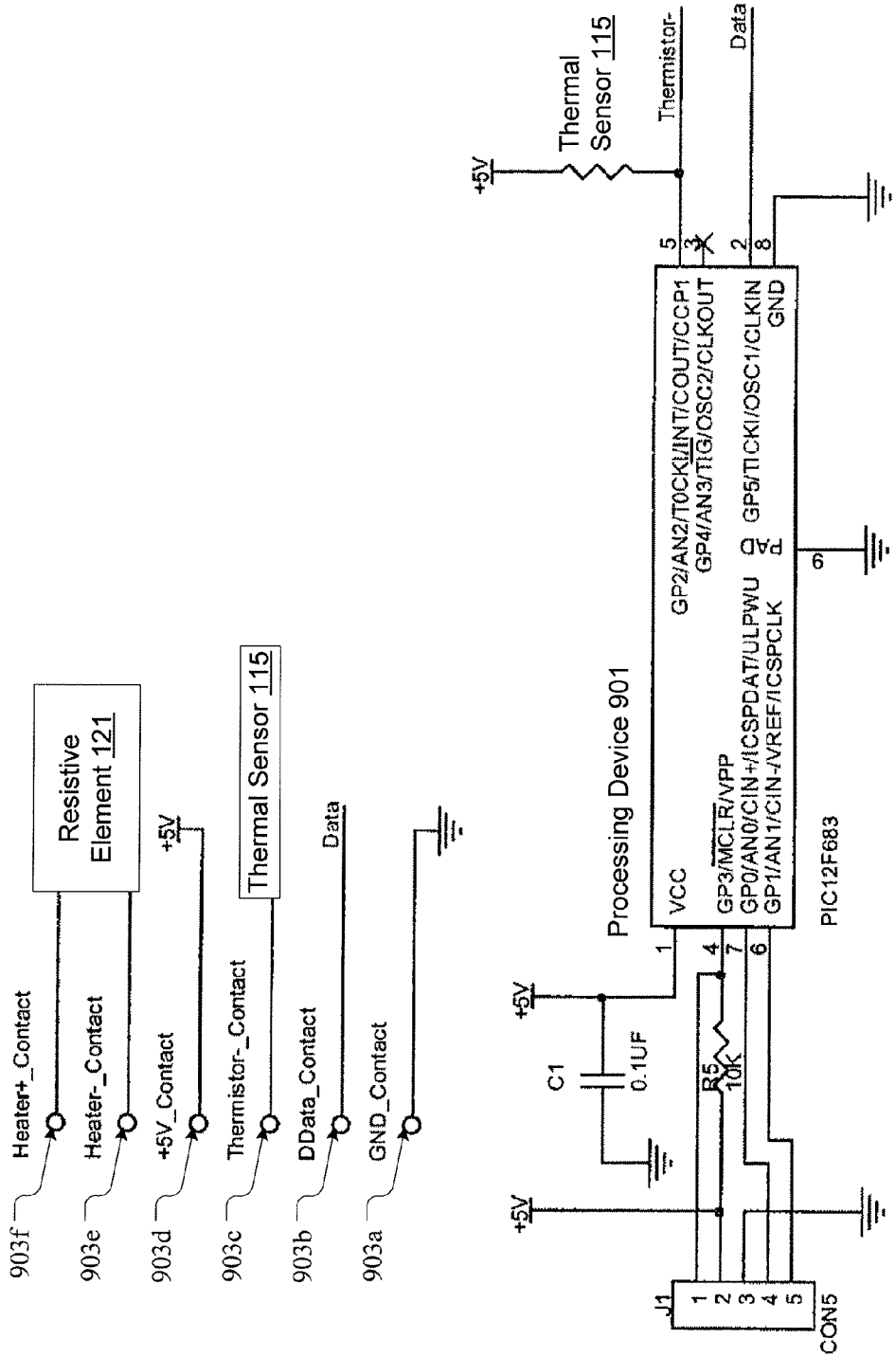

FIGS. 11*a-b* illustrate an embodiment with a second processing device 901 (e.g., located on tip segment 105) to receive temperature information from a first thermal sensor 115. In some embodiments, the second processing device 901 may convert signals from the first thermal sensor 115 (e.g., signals such as a change in voltage, current, resistance, etc. that is indicative of a change in temperature) to a first processing device 119 (e.g., on dispensing assembly 111). In some embodiments, a first thermal sensor 115 may be monitored by a second processing device 901 (which may be a PIC10/12 microprocessor) local to the temperature control layer 107. The second processing device 901 may receive signals (e.g., analog signals) from the first thermal sensor 115 and may analyze/convert these signals before communicating with the first processing device 119. For example, the second processing device 901 may send digital signals with temperature information (e.g., from the first thermal sensor 115) to the first processing device 119. The first processing device 119 may also receive other temperature information (e.g., as an analog signal from a second thermal sensor 117 as discussed above with respect to FIGS. 7*a-b*). In some embodiments, both signals (from the first and second thermal sensors) may be digital (or both may be analog). The first processing device 119 may compare the temperature information from the second processing device 901 and the temperature information received from the second thermal sensor 117 to determine if there is an offset between the temperatures detected by the thermal sensors (or, for example, between detected voltages indicative of temperature). Using temperature information from two different thermal sensors may allow the first processing device 119 to detect an in-series parasitic resistance located on the power, ground, or thermal sensor contact lines (e.g., thermistor contact lines) that may cause a discrepancy between the two signals (e.g., the digital signal and the analog signal). The first and/or second processing devices may try to compensate for the discrepancy if the discrepancy is small (such as <5 degrees Celsius) (e.g., by controlling/adjusting the resistive element 121 of the temperature control layer 107 using an average of the temperatures indicated by the first and second thermal sensors) or may indicate an error and/or shut down the ophthalmic medical device 100.

In some embodiments, the thermal sensors and/or second processing device 901 may communicate with first processing device 119 at least in part through connectors/contacts (e.g., between the tip segment 105 and the dispensing assembly 111). Connectors/contacts (e.g., connectors/contacts 701a,b and 903a-f) may be incorporated at least partially in the dispensing assembly interface connector 553 (other locations are also contemplated).

In some embodiments, first processing device 119 may be communicatively coupled to a memory 1050 (which may be an embedded/on-chip memory and/or a memory external to first processing device 119). Other locations for the memory are also contemplated (e.g., as an on-chip memory to second processing device 901). In some embodiments, the memory may be a static memory and the information on the memory 1050 may be accessed digitally. The memory may hold information such as number of times the tip segment 105 has been used, a temperature set point (e.g., a desired temperature to heat the drug to), drug delivery speed, drug density, drug thermal coefficients of expansion, etc. By storing the number of uses on the memory 1050, this information may be used to determine whether to allow the tip segment 105 to function (e.g., the tip segment 105 may be prevented from functioning if the number of uses exceeds a predetermined threshold (e.g., 1 use)). Using a memory may eliminate the need for a high current circuit/fuse (although, a fuse 601 may be also be used). Information stored on the memory 1050 may also be used in the operation of the tip segment 105 and/or dispensing assembly 111 (e.g., set-point temperature, expel velocities, volumes and disposable tip identification, etc). In some embodiments, a programming/debugging pin 1101 may be used to store information onto the second processing device 901 (e.g., onto an on-chip memory of second processing device 901) and/or to program the second processing device 901. For example, an external device such as a computer system may couple to the programming/debugging pin 1101 to interface with the second processing device 901 (and/or memory accessible to the second processing device 901).

Figure 12:
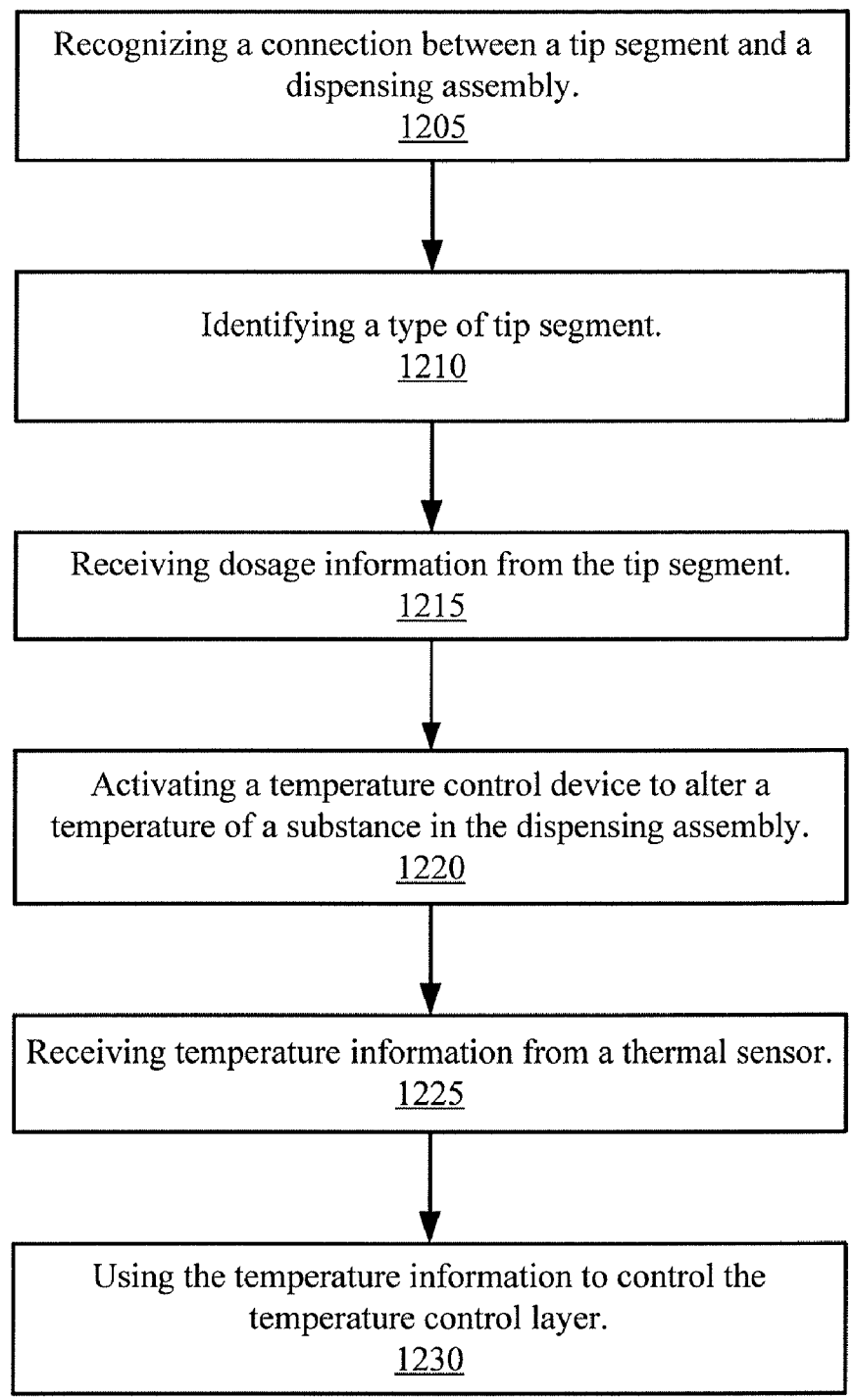
FIG. 12 illustrates a flowchart of an embodiment of a method for injecting a substance into an eye.

FIG. 12 illustrates a flowchart of an embodiment of a method for injecting a substance 123 into an eye 131. The method of FIG. 12 includes activating the temperature control layer 107 to heat or cool the substance 123 located in the dispensing chamber 103. The elements provided in the flowchart are illustrative only. The provided elements may be omitted, additional elements may be added, and/or various elements may be performed in a different order than provided below.

At 1205, a connection between a tip segment 105 and a dispensing assembly 111 may be recognized. For example, processing device 119 may send and/or receive signals from the tip segment 105 through connectors/contacts 701a,b and/or 903a-f. In some embodiments, components of tip segment 105 (such as processing device 901) may send signals to the processing device 119 when the tip segment 105 is coupled to the dispensing assembly 111.

At 1210, the type of tip segment 105 may be identified. For example, information may be stored on memory 1050 as to the type (e.g., single use, limited reuse, etc.) of tip segment 105 and this information may be passed to the processing device 119 when the tip segment 105 is coupled to the dispensing assembly 111.

At 1215, dosage information may be received from the tip segment 105. For example, dosage information (e.g., volume, dispense rate, etc.) may be stored on memory 1050 and be passed to the processing device 119 when the tip segment 105 is coupled to the dispensing assembly 111.

At 1220, a temperature control layer 107 may be activated to alter a temperature of a substance 123 contained in the dispensing chamber 103. In some embodiments, the temperature control layer 107 may be charged by an internal power source and/or may be charged by an external charging stand.

At 1225, temperature information (e.g., a change in voltage, current, resistance, etc. that is indicative of a change in temperature) may be received from a thermal sensor (such as thermal sensor 115 and/or 117). As another example, temperature information may be received in the form of a voltage or current detected from a bridge that includes the first and second thermal sensor (e.g., see FIG. 7c).

At 1230, the temperature information may be used to control the temperature control layer 107. For example, the processing device 119 may signal temperature control layer 107 to provide current to the resistive element 121 until a set temperature is indicated by one or more thermal sensors.

Figure 13:
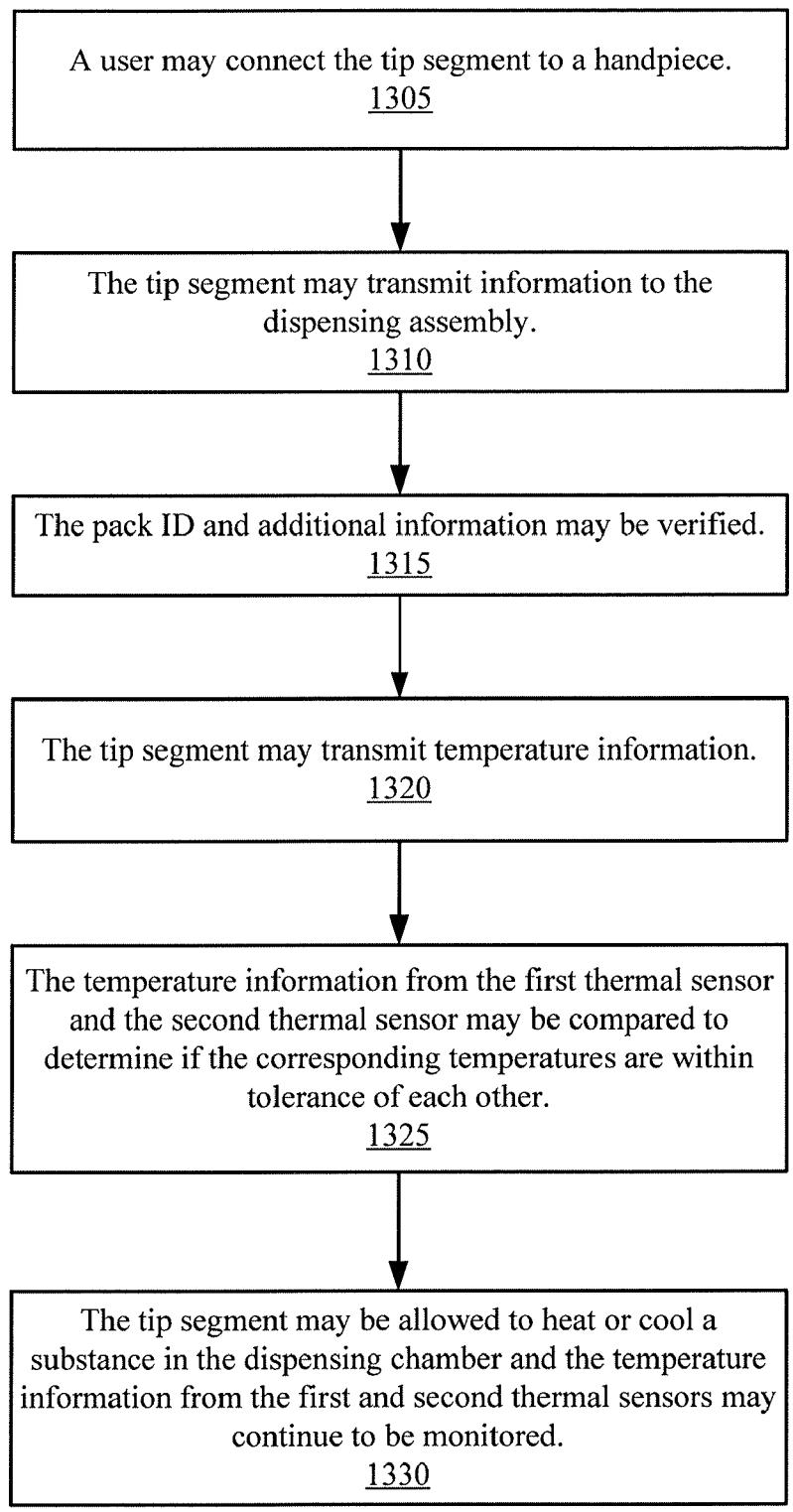
FIG. 13 illustrates a flowchart of an embodiment of a method for using temperature information from thermal sensors coupled to a handpiece.

FIG. 13 illustrates a flowchart of an embodiment of a method for operating the tip segment 105 and dispensing assembly 111 for injecting a substance 123 into the eye 131. The elements provided in the flowchart are illustrative only. The provided elements may be omitted, additional elements may be added, and/or various elements may be performed in a different order than provided below.

At 1305, a user may connect the tip segment 105 to a handpiece (e.g., a reusable handpiece including the dispensing assembly 111).

At 1310, the tip segment 105 (e.g., second processing device 901 on tip segment 105) may transmit information to the dispensing assembly 111 (e.g., to first processing device 119). The information may include pack identification (ID) (identifying a package the tip segment 105 was delivered in), procedural parameters (e.g., temperature set point, drug delivery speed, drug density, drug thermal coefficients of expansion, etc.), and number of prior uses (or, for example, information indicating that the tip segment 105 has not been used prior).

At 1315, the pack ID and additional information may be verified (e.g., by the first processing device 119 on the dispensing assembly 111). If the number of prior uses exceeds a predetermined threshold or if the information received (or not received) indicates a problem (e.g., does not fall within predetermined ranges), the dispensing assembly 111 (e.g., the first processing device 119) may indicate that the tip segment 105 should not be used. For example, if the ophthalmic injection device 100 is a limited reuse assembly and information stored in the memory 1050 indicates the tip segment 105 has been used more than a predetermined threshold (e.g., 1 time), the first processing device 119 may transmit a command to the second processing device 901 to shut down the tip segment 105 and/or prevent the tip segment's use.

At 1320, the tip segment 105 may transmit temperature information. For example, the second processing device 901 may monitor a first thermal sensor 115 and may send information indicative of temperature information received from the first thermal sensor (e.g., in digital form) to first processing device 119. Additional temperature information (e.g., from a second thermal sensor) may be transmitted to the first processing device 119 directly (e.g., in analog form (or digital form)).

At 1325, the temperature information from the first thermal sensor 115 and the second thermal sensor 117 may be compared to determine if the indicated temperatures are within tolerance of each other (e.g., within +/−0.5 degrees, +/−1 degrees, +/−5 degrees, +/−10 degrees, etc). In some embodiments, the temperature information may be separately compared to predetermined thresholds instead of being compared to each other. Other comparisons are also contemplated. For example, as seen in FIG. 7c, information (e.g., relayed through a detected voltage or current) from a bridge circuit including the first and second thermal sensor may be indicative of a difference between the two sensors.

At 1330, the tip segment 105 may be allowed to heat or cool a substance 123 in the dispensing chamber 103 and the temperature information from the first and second thermal sensors may continue to be monitored. If the detected temperatures are not found to be within a tolerance of each other or separately within a predetermined range, the tip assembly 105 may be instructed not to initiate heating or cooling a substance 123 in the dispensing chamber 103 and/or the tip assembly 105 may discontinue heating or cooling substance 123 if the heating/cooling process has already started. In some embodiments, an error may be indicated if the detected temperatures are not within a tolerance. If the heating/cooling sequence had started, a use of the tip segment 105 may be indicated on a memory 1050 accessible by the second processing device 901 and/or first processing device 119 at startup. The indicated use may prevent the tip segment 105 from being used again in the future.

Figure 14:
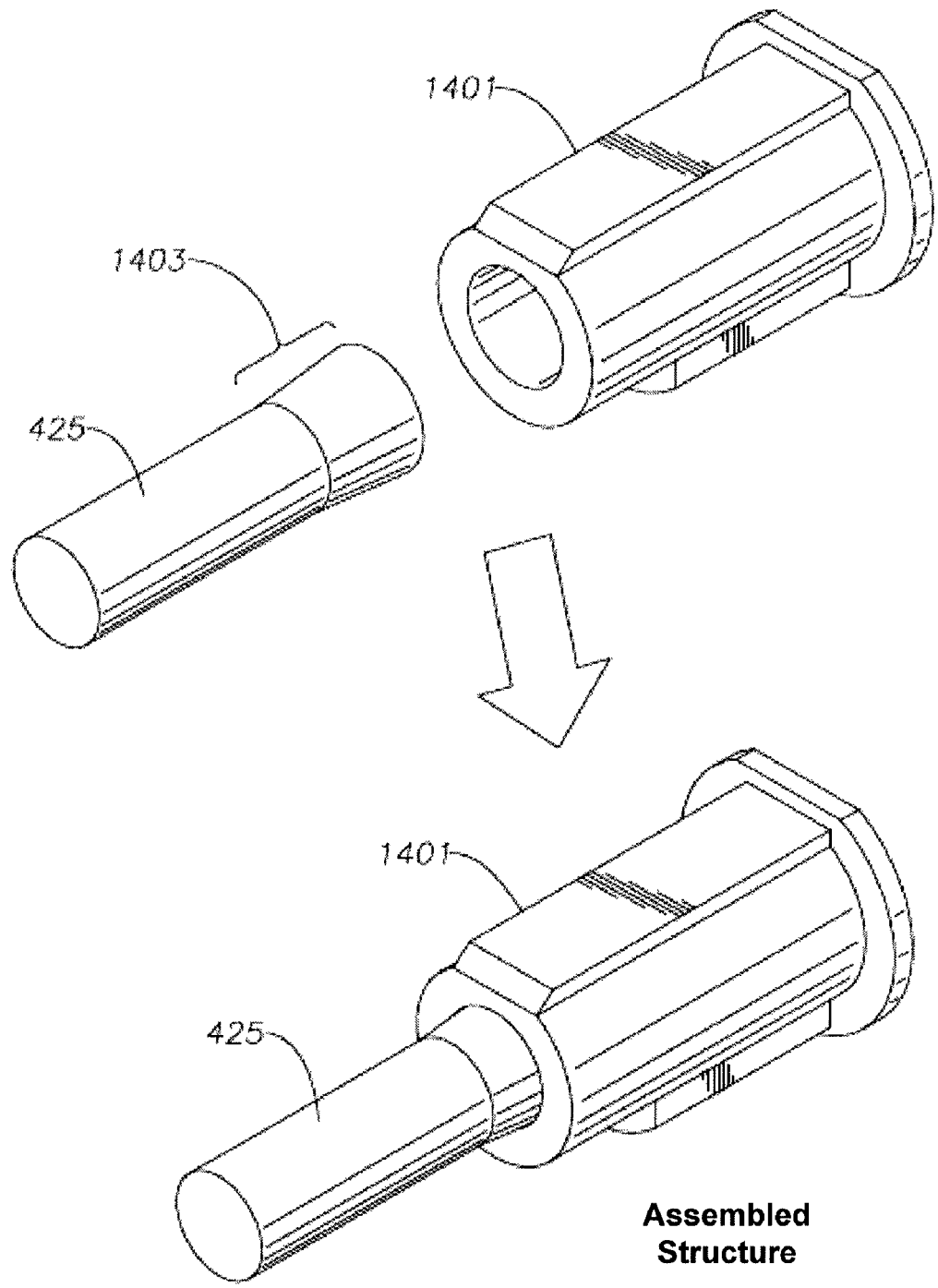
FIG. 14 illustrates coupling the inner dispenser assembly to an outer support, according to an embodiment.

FIG. 14 illustrates an embodiment of coupling the dispensing chamber housing 425 to an outer support 1401. In some embodiments, the outer support 1401 may be an elastomer support (other materials such as metal may also be used) that is separately coupled inside the tip housing 215. The dispensing chamber housing 425 may include a bell-shaped end 1403 that secures the end of the dispensing chamber housing 425 inside the support 1401. For example, one end of the dispensing chamber housing 425 may fit through the outer support while the bell-shaped end 1403 may hold the dispensing chamber housing 425 in place (e.g., through a friction fit (or, for example, through adhesive) with the support 1401. The dispensing chamber housing 425 may be coupled inside the support 1401 using other mechanisms (e.g., adhesives, fasteners, ultrasonic welding, etc).

Figure 15:
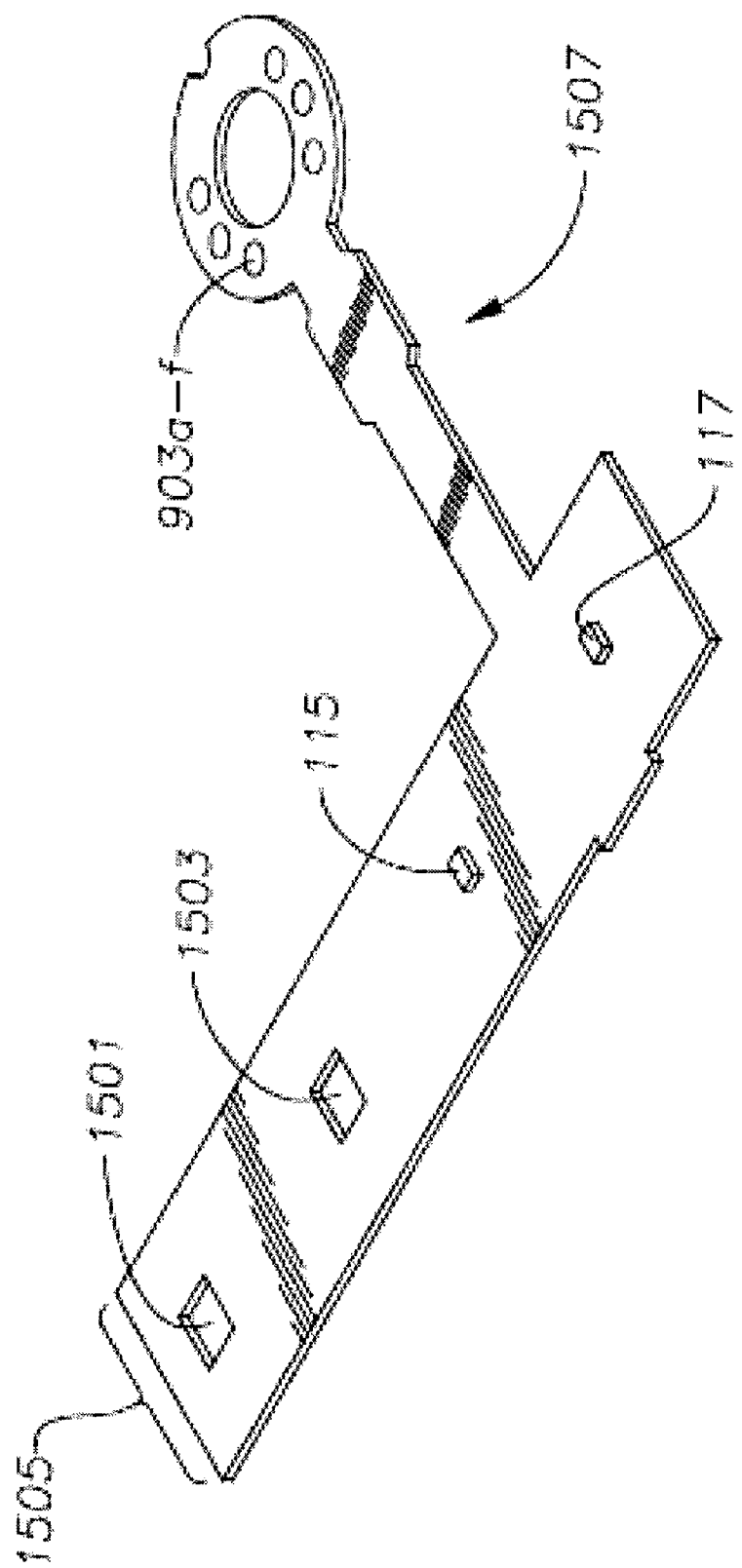
FIG. 15 illustrates another embodiment of the thermal feedback layer.

FIG. 15 illustrates another embodiment of the thermal feedback layer 1507. In the embodiment shown in FIG. 15, the thermal feedback layer 1507 may not include a processing tab segment holding second processing device 901. For example, the processing device 901 may be included on the tab portion 1505 (or may not be included). In some embodiments, the thermal sensors 115/117 may be placed further apart on the thermal feedback layer 1507 and two windows 1501/1503 may be provided (one for each thermal sensor) for the wrap around (see FIGS. 16a-d). The circular contact portion may include contacts 903a-f on one layer to interface with corresponding contacts on the lower dispensing assembly 111e (which, as seen in FIG. 16d, may include multiple corresponding contacts). In some embodiments, the lower dispensing assembly 111e may include six corresponding interface connectors 1653a-f (see example interface connector 553 and example dispenser assembly components in FIG. 5). Other configurations are also possible (e.g., data from the six connectors may be placed through a single connector interface with the lower dispenser assembly).

Figure 16A:
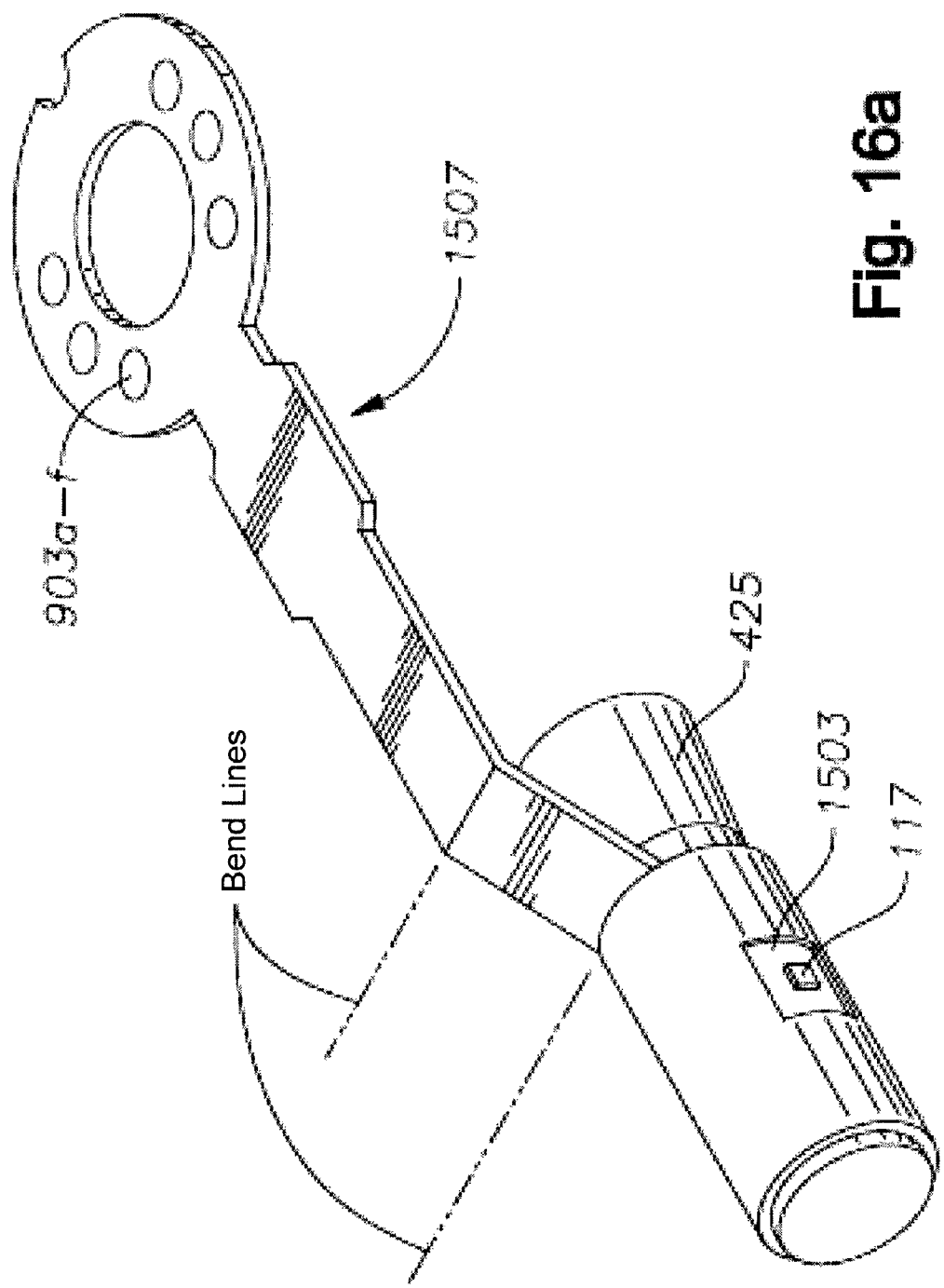
FIGS. 16a-d illustrate an example of assembling the thermal feedback layer in the dispenser assembly.
Figure 16B:
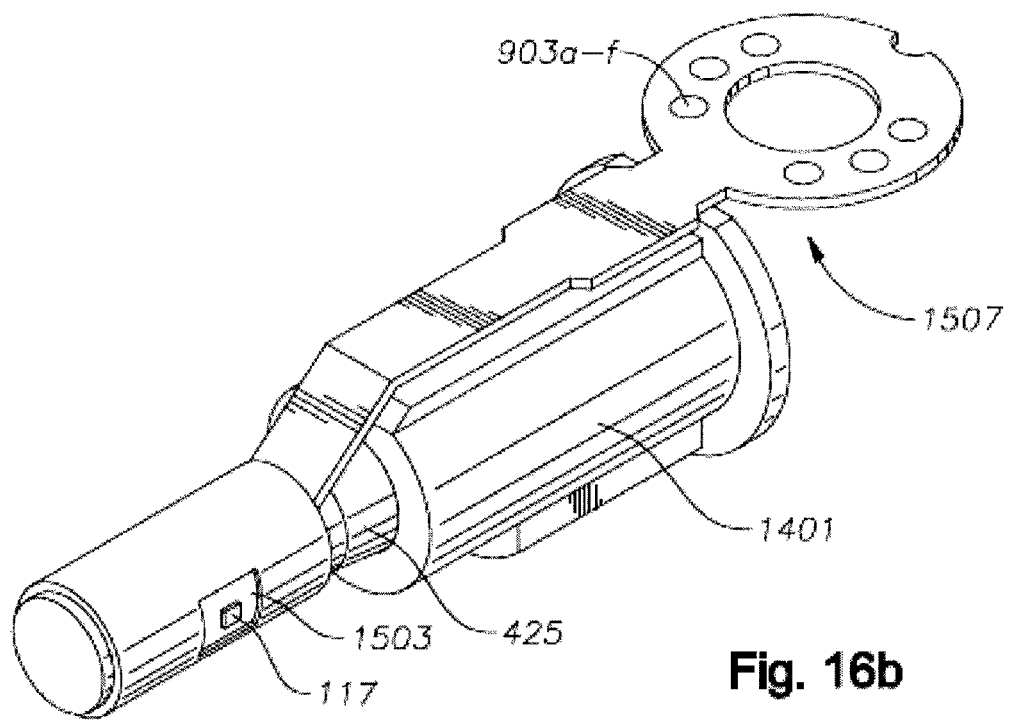
Figure 16C:
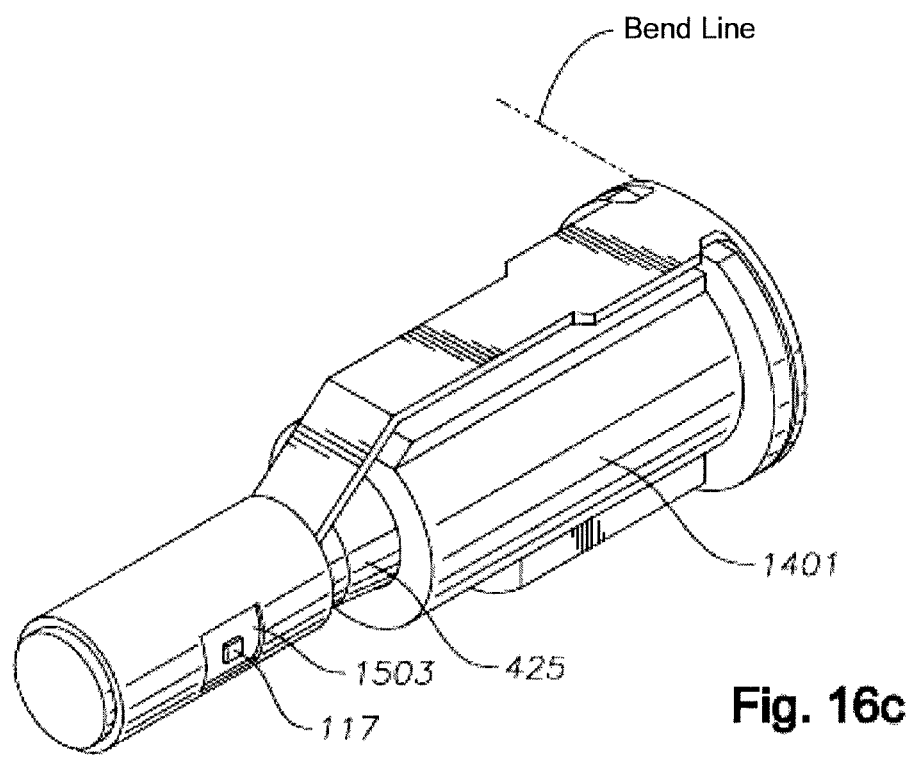
Figure 16D:
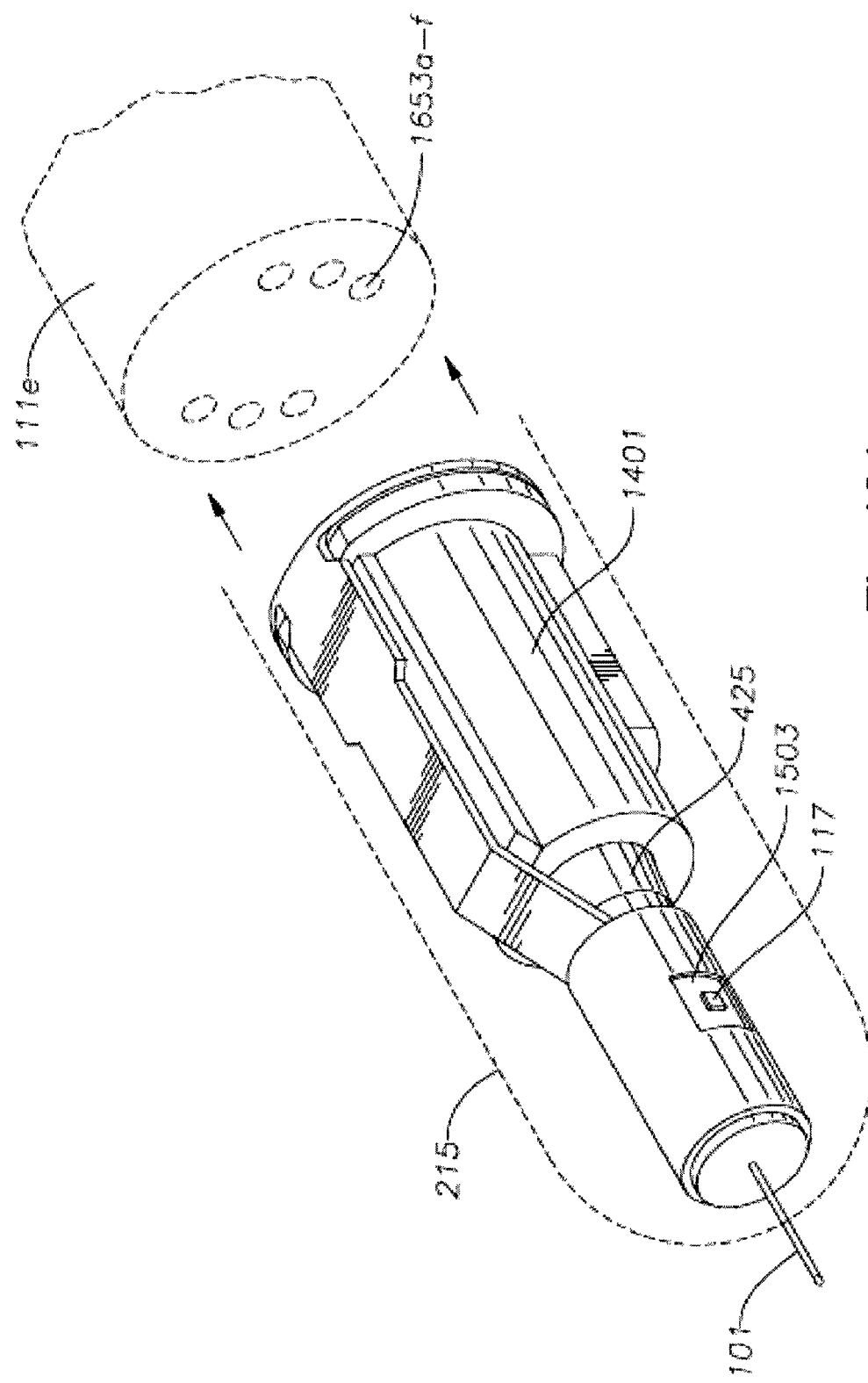

FIGS. 16a-d illustrate an example of assembling the thermal feedback layer 1507 into the dispenser assembly. As seen in FIG. 16a, the tab portion 1505 of thermal feedback layer 1507 may be wrapped around the dispensing chamber housing 425 such that a thermal sensor 115/117 lines up on alternate sides of the dispensing chamber housing 425 and windows 1501/1503 line up with their corresponding thermal sensor 115/117 such that each thermal sensor 115/117 protrudes through respective windows 1501/1503. In some embodiments, the bottom of the thermal feedback layer 1507 may be coated with an adhesive. In some embodiments, a backing may be peeled off of the thermal feedback layer 1507 to expose the adhesive prior to wrapping the thermal feedback layer 1507 on the dispensing chamber housing 425. Other fasteners are also contemplated (e.g., clips, welds, etc). As seen in FIG. 16b, the thermal feedback layer 1507 may bend along a contour of the support 1401. As seen in FIG. 16c, the circular contact portion may also bend to attach to the back of the support 1401 to align the contacts 903a-f with corresponding connectors 1653a-f (which may themselves be contacts) on the dispensing assembly 111e. In some embodiments, contacts 903a-f may be electrically connected to various components on the thermal feedback layer 1507 (e.g., the thermal sensors 115/117) through electrical lines embedded/deposited on the thermal feedback layer 1507. In some embodiments, electrical signals may travel through the contacts 903a-f and connectors 1653a-f to allow the dispenser 111e to communicate with the components of the thermal feedback layer 1507 (or other layers such as the temperature control layer 107 which may also communicate through corresponding contacts (e.g., contacts 903e-f shown in FIG. 9b)). As seen in FIG. 16d, the dispensing chamber housing 425 may be inserted into tip assembly 215 which may be coupled to the dispensing assembly 111e (to mate connectors 1653a-f and contacts 903a-f). As seen in FIG. 2, in some embodiments, the tip assembly 215 may be screwed onto the dispensing assembly 111e (other attachment mechanisms are also contemplated).

In some embodiments, the tip segment 105 and/or dispensing assembly 111 may include one or more processing devices (e.g., first processing device 119, second processing device 901, etc). In various embodiments, the processing devices may include integrated circuits with power, input, and output pins capable of performing logic functions. For example, first processing device 119 may be a targeted device controller that performs specific control functions targeted to one or more devices or components, such as temperature control layer 107 or power source 505. In some embodiments, first processing device 119 may directly control temperature control layer 107 or may interface with another processing device (such as a temperature control layer controller on the temperature control layer 107) to control the basic functionality of the temperature control layer 107. While depicted as one component in various FIGs., processing devices (such as first processing device 119, second processing device 901, etc.) may each be made of many different components or integrated circuits. For example, each processing device may include a single processing device or a plurality of processing devices.

The processing devices may include a microprocessor (e.g., a programmable microprocessor), controller (such as a micro-controller or other special purpose controller), digital signal processor, microcomputer, central processing unit, field programmable gate array, programmable logic device, state machine, logic circuitry, control circuitry, analog circuitry, digital circuitry, and/or any device that manipulates signals (analog and/or digital) based on operational instructions. A memory coupled to and/or embedded in the processing devices may be a single memory device or a plurality of memory devices. Such a memory device may be a read-only memory, random access memory, volatile memory, non-volatile memory, static memory, dynamic memory, flash memory, cache memory, and/or any device that stores digital information. Note that when the processing devices implement one or more of its functions via a state machine, analog circuitry, digital circuitry, and/or logic circuitry, the memory storing the corresponding operational instructions may be embedded within, or external to, the circuitry comprising the state machine, analog circuitry, digital circuitry, and/or logic circuitry. The memory 1003 may store, and the processing devices may execute, operational instructions corresponding to at least some of the elements illustrated and described in association with the figures.

Various modifications may be made to the presented embodiments by a person of ordinary skill in the art. For example, although some of the embodiments are described above in connection with surgical handpieces, it can also be used with other surgical devices utilizing a heater element. Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. An ophthalmic injection device, comprising: a dispensing chamber configured to hold a substance to be injected into an eye; a thermal feedback layer comprising at least one thermal sensor; a temperature control layer configured to apply or remove heat from the dispensing chamber; wherein the thermal feedback layer and the temperature control layer are coupled to the dispensing chamber, wherein each of the thermal feedback layer and the temperature control layer are flexible and configured to at least partially wrap around the dispensing chamber; and wherein the thermal feedback layer has a form factor that includes a thermal sensor on a first tab and a microprocessor on a second tab connected to the first tab.

2. The ophthalmic injection device of claim 1, wherein the thermal feedback layer and the temperature control layer have an identical form factor.

3. The ophthalmic injection device of claim 1, wherein the temperature control layer comprises resistive traces on a third tab oriented to overlap the first tab of the thermal feedback layer when the thermal feedback layer and the temperature control layer are coupled to the dispensing chamber.

4. The ophthalmic injection device of claim 3, wherein the temperature control layer does not have a tab corresponding to the second tab of the thermal feedback layer.

5. The ophthalmic injection device of claim 1, wherein the thermal feedback layer comprises traces made of copper, silver, or gold and the thermal feedback layer comprises traces made of inconel.

6. The ophthalmic injection device of claim 1, wherein the thermal feedback layer and the temperature control layer are configured to be bonded together to form one assembly that is configured to be wrapped at least partially around the dispensing chamber.

7. The ophthalmic injection device of claim 1, wherein the dispensing chamber comprises a first end face, a second end face, and a side face coupling the first end face and the second end face, and wherein at least one of the thermal feedback layer and the temperature control layer are configured to cover more than 50 percent of the side face.

* * * * *